US012606569B2

(12) United States Patent
Ford et al.

(10) Patent No.: US 12,606,569 B2
(45) Date of Patent: Apr. 21, 2026

(54) ALKALOID-CONTAINING COMPOSITIONS AND USES THEREOF

(71) Applicant: Biotelliga Holdings Limited, Auckland (NZ)

(72) Inventors: Stephen Ford, Auckland (NZ); Emilie Galand, Auckland (NZ); Bernard Cecil Kimble, Auckland (NZ); Alan James Robinson, Auckland (NZ); Roelof Van Ginkel, Auckland (NZ)

(73) Assignee: Biotelliga Holdings Limited, Auckland (NZ)

( * ) Notice: Subject to any disclaimer, the term of this patent is extended or adjusted under 35 U.S.C. 154(b) by 710 days.

(21) Appl. No.: 16/622,850

(22) PCT Filed: Jun. 15, 2018

(86) PCT No.: PCT/IB2018/054406
§ 371 (c)(1),
(2) Date: Dec. 13, 2019

(87) PCT Pub. No.: WO2018/229717
PCT Pub. Date: Dec. 20, 2018

(65) Prior Publication Data

US 2020/0199139 A1 Jun. 25, 2020

(30) Foreign Application Priority Data

Jun. 16, 2017 (NZ) ........................................ 732930

(51) Int. Cl.

| | |
|---|---|
| ***C07D 491/18*** | (2006.01) |
| ***A01G 13/00*** | (2006.01) |
| ***A01N 25/02*** | (2006.01) |
| ***A01N 25/22*** | (2006.01) |
| ***A01N 43/90*** | (2006.01) |

(52) U.S. Cl.
CPC ........... *C07D 491/18* (2013.01); *A01G 13/00* (2013.01); *A01N 25/02* (2013.01); *A01N 25/22* (2013.01); *A01N 43/90* (2013.01)

(58) Field of Classification Search
CPC ...... C07D 491/18; A01N 25/02; A01N 25/22; A01N 43/90; A01G 13/00
See application file for complete search history.

(56) References Cited

U.S. PATENT DOCUMENTS

| | | | | |
|---|---|---|---|---|
| 4,061,740 A * | 12/1977 | Boatright | ............... | A01N 25/02 514/97 |
| 5,185,028 A | 2/1993 | Powell et al. | | |
| 2009/0227453 A1 | 9/2009 | Bell et al. | | |
| 2010/0235950 A1* | 9/2010 | Pennell | .................. | A01N 43/90 514/230.2 |
| 2011/0086848 A1* | 4/2011 | Stork | ..................... | A01N 25/30 514/342 |

FOREIGN PATENT DOCUMENTS

| | | | |
|---|---|---|---|
| DE | 4112873 A1 | 10/1992 | |
| WO | WO-9917608 A1 * | 4/1999 | ............. A01N 25/30 |
| WO | WO 2008/111861 | 9/2008 | |
| WO | WO 2016/091987 | 6/2016 | |
| WO | WO-2016091987 A1 * | 6/2016 | ............. A01N 65/44 |
| WO | WO 2017/191095 A1 | 11/2017 | |
| WO | WO 2018/229717 | 12/2018 | |

OTHER PUBLICATIONS

Extended European Search Report, dated Feb. 23, 2021, corresponding to European Application No. EP 18 81 8507, 2 pages.
Riedell et al. (1991) "Naturally-Occurring and Synthetic Loline Alkaloid Derivatives: Insect Feeding Behavior Modification and Toxicity," J. Entomol. Sci. 26(1), 122-129.
Becke (1993) "Density-functional thermochemistry. III. The role of exact exchange," Journal of Chemical Physics, 98, 5648-5652.
Deuri et al. (2012) "A DFT study on nucleophilicity and site selectivity of nitrogen nucleophiles," Computational and Theoretical Chemistry, 980, 49-55 (Abstract only) (Abstract only).
Domingo et al. (2008) "Understanding the Reactivity of Captodative Ethylenes in Polar Cycloaddition Reactions. A Theoretical Study," Journal of Organic Chemistry 73, 4615-4624.
International Search Report and Written Opinion, dated Sep. 27, 2018, corresponding to International Application No. PCT/IB2018/054406, from which the present application claims priority, 9 pp.
Jaramillo et al. (2008) "A further exploration of a nucleophilicity index based on the gas-phase ionization potentials," Journal of Molecular Structure: Theochem, 865, 68-72.
Johnson et al. (1985) "Insect Feeding Deterrents in Endophyte-Infected Tall Fescue," Applied and Environmental Microbiology, vol. 49, No. 3, 568-571.
Lee et al. (1988) "Development of the Colle-Salvetti correlation-energy formula into a functional of the electron density," Physical Review B, 37, 785-789.

(Continued)

*Primary Examiner* — Ali Soroush
*Assistant Examiner* — Andriae M Holt
(74) *Attorney, Agent, or Firm* — Leydig, Voit & Mayer, Ltd.

(57) ABSTRACT

The present invention provides compositions comprising loline alkaloids including pesticidal compositions, methods of producing the compositions and uses of the compositions including uses as control agents. Methods for the control of pests, including plant or animal pests, for the enhancement of plant growth or reproduction, and treatment and prevention of insect infection and infestation, for example in plants or animals, are also provided.

24 Claims, 2 Drawing Sheets

(56) References Cited

OTHER PUBLICATIONS

Perez et al. (2009) “A condensed-to-atom nucleophilicity index. An application to the director effects on the electrophilic aromatic substitutions,” Journal of Molecular Structure: Theochem, 895, 86-91.

Reed et al. (1988) “Intermolecular interactions from a natural bond orbital, donor-acceptor viewpoint,” Chemical Review, 88, 899-926.

* cited by examiner

ALKALOID-CONTAINING COMPOSITIONS AND USES THEREOF

CROSS-REFERENCE TO RELATED APPLICATIONS

This application is a U.S. National Stage Application filed under 35 U.S.C. § 371 of International Application No. PCT/IB2018/054406, filed Jun. 15, 2018, which claims the benefit of New Zealand Application No. 732930, filed Jun. 16, 2017. Both of these applications are hereby incorporated by reference in their entireties.

PARTIES TO A JOINT RESEARCH AGREEMENT

The presently claimed invention was made by or on behalf of the below listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are: Biotelliga Holdings Ltd. and Syngenta Crop Protection AG.

FIELD OF THE INVENTION

The present invention relates generally to the field of biology, more particularly to compositions comprising loline alkaloids including pesticidal compositions, methods of producing the compositions and uses of the compositions including uses as control agents. Methods for the control of pests, including plant or animal pests, and for the enhancement of plant growth or reproduction, and treatment and prevention of insect infection and infestation, for example in plants or animals, are also provided.

BACKGROUND TO THE INVENTION

Loline alkaloids are produced symbiotically during infection of grasses or in axenic culture by fungi, particularly *Epichloë* species (which, following a nomenclature realignment, now includes the previously separate anamorph *Neotyphodium* spp.).

To the applicant's knowledge, there are no reports of the successful use of compositions comprising loline alkaloids as pesticides in the agricultural, horticultural, medical or veterinary fields.

It is an object of the present invention to provide compositions comprising loline alkaloids, particularly N-formylloline, having good stability which meet this need, or which at least provide the public with a useful choice.

Other objects of the invention may become apparent from the following description which is given by way of example only.

SUMMARY OF THE INVENTION

In one aspect the invention provides a composition comprising at least about 10 g/L of one or more loline alkaloids having the structure of Formula [I]:

[I]

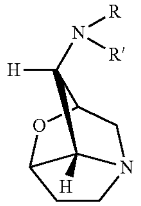

wherein R═H or $CH_3$ and R'═H, $CH_3$, CHO or $COCH_3$, the one or more loline alkaloids comprising N-formylloline having the structure of Formula [II]:

[II]

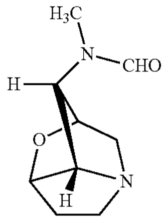

and one or more solvents; wherein a) the molar ratio of total hydroxyl groups and nitrogen-containing groups to N-formylloline of the composition is less than about 20, or
b) the molar ratio of total hydroxyl groups and nitrogen-containing groups to N-formylloline of the composition is greater than about 20, and wherein the nucleophilicity coefficients of the hydroxyl groups or nitrogen-containing groups of the composition are less than about 0.6 eV;

wherein the nitrogen-containing groups are selected from ammonia, a primary amine group, a secondary amine group, or mixtures thereof.

In another aspect, the invention provides a composition comprising N-formylloline (NFL) having the structure of Formula [II]:

[II]

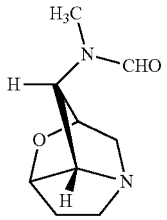

and one or more solvents; wherein a) the molar ratio of total hydroxyl groups and nitrogen-containing groups to N-formylloline in the composition is equal to or less than about 20; or
b) the molar ratio of total hydroxyl groups and nitrogen-containing groups to N-formylloline in the composition is greater than about 10 or about 20, preferably less than about 40, about 35, or about 30, and the nucleophilicity coefficient of the hydroxyl groups and nitrogen-containing groups in the composition is less than about 0.6 eV, preferably 0.55 eV, more preferably less than about 0.5 eV, wherein the nitrogen-containing groups are selected from ammonia, a primary amine group, a secondary amine group, or a combination of any two or more thereof.

In one embodiment, the molar ratio of total hydroxyl groups and nitrogen-containing groups to N-formylloline in the composition is equal to or less than about 20, 19, 18, 17, 16, 15, 14, 13, 12, 11, or 10, and useful ranges may be selected between any of these values.

In one embodiment, the molar ratio of total hydroxyl groups and nitrogen-containing groups to N-formylloline in the composition is greater than about 20, preferably less than about 40, about 35, or about 30, and the nucleophilicity coefficient of the hydroxyl groups and nitrogen-containing groups in the composition is less than about 0.55 eV, preferably less than about 0.5 eV.

In one embodiment, the molar ratio of total hydroxyl groups and nitrogen-containing groups to N-formylloline in the composition is greater than about 20, preferably less than about 40, about 35, or about 30, and the nucleophilicity coefficient of the hydroxyl groups and nitrogen-containing groups of the one or more solvents is less than about 0.3 eV.

In one embodiment, the molar ratio of total hydroxyl groups and nitrogen-containing groups to N-formylloline in the composition is greater than about 10, preferably less than about 40, 35, 30, 25, or 20, and the nucleophilicity coefficient of the hydroxyl groups or nitrogen-containing groups of the one or more solvents is less than about 0.3 eV.

In one embodiment, the composition is aqueous. In another embodiment, the composition is aqueous, and the nucleophilicity coefficient of the hydroxyl groups or nitrogen-containing groups of the one or more solvents is less than about 0.6 eV, preferably less than about 0.55 eV, preferably less than about 0.5 eV.

In one embodiment the concentration of N-formylloline present in the composition is reduced by less than about 10% when stored at 20° C. (at 1 atm) for at least two years. In another embodiment the concentration of N-formylloline present in the composition is reduced by less than about 10% when stored at 54° C. (at 1 atm) for at least two weeks.

In another aspect, the invention provides a composition comprising N-formylloline having the structure of formula [II]

[II]

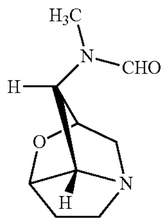

and one or more solvents, wherein the concentration of N-formylloline present in the composition is reduced by less than about 10% when stored at 20° C. (at 1 atm) for at least two years.

In another aspect the invention provides a composition comprising at least about 10 g/L of one or more loline alkaloids having the structure of Formula [I]:

[I]

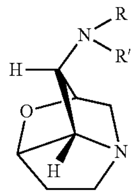

wherein R=H or $CH_3$ and R'=H, $CH_3$, CHO or $COCH_3$, the one or more loline alkaloids comprising at least partially purified or isolated N-formylloline having the structure of Formula [II]:

[II]

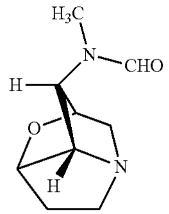

and one or more solvents, wherein the concentration of N-formylloline present in the composition is reduced by less than about 10% when stored at 54° C. (at 1 atm) for at least two weeks.

In various embodiments, the concentration of N-formylloline present in the composition is reduced by less than about 10%, for example when stored at 20° C. (at 1 atm) for at least two years, 35° C. for at least 12 weeks, at 40° C. for at least eight weeks, or at 54° C. for at least two weeks.

In one embodiment, a) the molar ratio of total hydroxyl groups and nitrogen-containing groups to N-formylloline of the composition is less than about 20, or b) the molar ratio of total hydroxyl groups and nitrogen-containing groups to N-formylloline of the composition is greater than 20, and wherein the nucleophilicity coefficients of the hydroxyl groups or nitrogen-containing groups of the composition are less than 0.55 eV;

wherein the nitrogen-containing groups are selected from ammonia, a primary amine group, a secondary amine group, or mixtures thereof.

Any one or more of following embodiments may relate to any of the aspects herein, above or below, in any combination.

In one embodiment, the composition further comprises one or more loline alkaloids of Formula [I]:

[I]

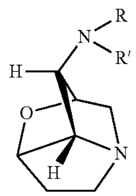

wherein R=H or $CH_3$ and R'=H, $CH_3$, CHO or $COCH_3$.

More specifically, Formula [I] includes:

1) loline where R=$CH_3$ and R'=H;
2) norloline where R=H and R'=H;
3) N-methylloline where R=$CH_3$ and R'=$CH_3$;
4) N-formylloline where R=$CH_3$ and R'=CHO;
5) N-formylnorloline where R=H and R'=CHO;
6) N-acetylloline where R=$CH_3$ and R'=$COCH_3$; and
7) N-acetylnorloline where R=H and R'=$COCH_3$.

In various embodiments, the composition comprises one or more loline alkaloids selected from the group consisting of loline, norloline, N-acetylloline (NAL), N-formylloline (NFL), N-acetylnorloline (NANL), and N-methylloline (NML), N-formylnorloline, or a combination of any two or more thereof. In one embodiment, the composition comprises N-acetylloline (NAL), N-formylloline (NFL), and N-acetylnorloline (NANL). In a particularly preferred embodiment the composition comprises N-acetylloline (NAL), N-formylloline (NFL), N-acetylnorloline (NANL), and loline.

In one embodiment, one or more of the one or more loline alkaloids are at least partially purified or isolated.

In one embodiment, the N-formylloline is at least partially purified or isolated.

In one embodiment, the composition comprises at least about 5, 10, 20, 30, 40, 50, 60, 70, 80, 90, 100, 200, 300, 400, 500, 600, 700, 800, 900, 1000, 2000, 3000, 4000, 5000, 6000 or 7000 g/L of N-formylloline having the structure of formula [II], and useful ranges may be selected between any of these values (for example, about 5 to about 7000, about 5 to about 700, about 10 to about 700, about 10 to about 7000, about 50 to about 500, about 50 to about 7000, about 100 to about 300, about 100 to about 7000, about 500 to about 700, or about 500 to about 7000 g/L).

In one embodiment, the composition comprises at least about 0.05, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60 or 70 w/w N-formylloline having the structure of formula [II], and useful ranges may be selected between any of these values (for example, about 0.05 to about 70, about 1 to about 70, about 1 to about 50, about 5 to about 50, about 10 to about 30, or about 50 to about 70%).

In one embodiment, the composition comprises at least about 10, 20, 40, 50, 60, 70, 80, 90, 100, 200, 300, 400, 500, 600, 700, 800, 900, 1000, 2000, 3000, 4000, 5000, 6000 or 7000 g/L of one or more loline alkaloids having the structure of Formula [I], and useful ranges may be selected between any of these values (for example, about 10 to about 7000, about 10 to about 700, about 50 to about 7000, about 50 to about 500, about 100 to about 7000, about 100 to about 300, about 500 to about 7000, or about 500 to about 700 g/L).

In one embodiment, the composition comprises at least about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, or 70% w/w loline alkaloids having the structure of formula [I], and useful ranges may be selected between any of these values (for example, about 0.1 to about 70, about 1 to about 70, about 1 to about 50, about 5 to about 50, about 10 to about 30, about 50 to about 70%).

In various embodiment the composition may comprise at least about 5, 6, 7, 8, 9, 10, 20, 30, 40, 50, 60, or 70% w/w of a loline alkaloid composition comprising loline alkaloids of formula [I], and useful ranges may be selected between any of these values (for example, about 5 to about 70, about 5 to about 50, about 10 to about 30, about 50 to about 70% w/w). In this embodiment the loline alkaloid composition may comprise at least about 20, 25, 30, 35, 40, 45, 50, 55, 60, 65, 70, 75, 80, 85, 90, 95, 99, or 100% w/w loline alkaloids of formula [I], and useful ranges may be selected between any of these values (for example, about 20 to about 100, about 30 to about 100, about 40 to about 100, about 50 to about 100, or about 60 to about 100% w/w). Relative amounts of individual loline alkaloids of formula [I] may comprise the amounts discussed above and below. Preferably the loline alkaloids of formula [I] are N-acetylnorloline (NANL), N-formylloline (NFL), and N-acetylloline (NAL). More preferably the loline alkaloid of formula [I] is N-formylloline.

In one embodiment, the N-formylloline having the structure of Formula [II] and/or the one or more loline alkaloids having the structure of Formula [I] are substantially pure. For example, the one or more loline alkaloids are substantially pure. In one example, the one or more loline alkaloids are from a non-synthetic source, for example, one or more substantially pure loline alkaloids from a non-synthetic source.

In one embodiment, the composition is substantially free of non-loline plant or fungal derived compounds or material.

In one embodiment, the composition consists essentially of N-formylloline, optionally together with one or more loline alkaloids of Formula [I], and one or more solvents. In a further embodiment, the composition consists of N-formylloline, optionally together with one or more loline alkaloids of Formula [I], and one or more solvents. In a further embodiment, the composition comprises N-formylloline as active ingredient, optionally together with one or more loline alkaloids of Formula [I], and one or more solvents.

In various embodiments the composition comprises N-acetylloline (NAL) having the structure of Formula [III]:

[III]

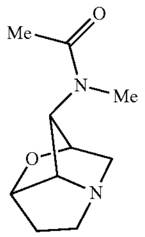

In various embodiments the composition comprises N-acetylnorloline (NANL) having the structure of Formula [IV]:

[IV]

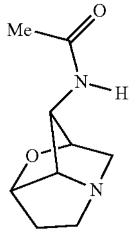

In various embodiments the composition comprises loline having the structure of Formula [V]:

[V]

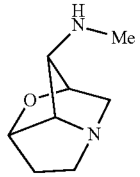

In one embodiment, the one or more loline alkaloids comprise at least about 1, 2, 3, 4, 5, 6, 7, 8, 9, 10, 20, 30, 40, 50, 60, or 70% w/w of the composition, and the composition comprises two or more loline alkaloids, for example two or more, or three or more loline alkaloids selected from the group comprising N-acetylloline (NAL), N-formylloline (NFL), N-acetylnorloline (NANL), and loline.

In another embodiment, the invention provides a composition comprising one or more loline alkaloids, wherein the one or more loline alkaloids have a purity of greater than about 95% pure. In one embodiment, the one or more loline alkaloids have a purity of greater than about 96% pure, a purity of greater than about 97% pure, a purity of greater than about 98% pure, a purity of greater than about 99% pure, or a purity of greater than about 99.5% pure.

In one embodiment one or more loline alkaloids in the composition have a purity of greater than about 95% pure, and the composition comprises two or more loline alkaloids, for example, two or more or three or more loline alkaloids selected from the group comprising N-acetylloline (NAL), N-formylloline (NFL), N-acetylnorloline (NANL), and loline.

In various embodiments the weight ratio of [NFL]:[NAL] in the composition or extract is less than about 20:1, about 18:1, about 17:1, about 16:1, 15:1, about 14:1, about 13:1, about 12:1, about 11:1, about 10:1, about 9:1, about 8:1, about 7:1, about 6:1, about 5:1, about 4:1, about 3:1, about 2:1, or about 1:1, and useful ranges may be selected between any of these values (for example, about 20:1 to about 1:1, about 15:1 to about 1:1, about 12:1 to about 2:1, about 10:1 to about 2:1, about 8:1 to about 2:1, or about 6:1 to about 2:1). In one embodiment, the weight ratio of [NFL]:[NAL] is about 4:1 or about 5:1.

In various embodiments the weight ratio of [NANL]:[NFL] in the composition or extract is greater than about 1:20, about 1:19, about 1:18, about 1:15, about 1:12, about 1:10, about 1:8, about 1:6, about 1:5, about 1:4, about 1:2, or about 1:1, and useful ranges may be selected between any of these values (for example, about 1:20 to about 1:1, about 1:15 to about 1:1, from about 1:12 to about 1:1, from about 1:10 to about 1:1, from about 1:8 to about 1:1, or about 1:8 to about 1:2. In one embodiment, the weight ratio of [NANL]:[NFL] is about 1:8. In one embodiment, the weight ratio of [NANL]:[NFL] is about 1:2.

In various embodiments the weight ratio of [NANL]:[NAL] in the composition or extract is greater than about 1:10, about 1:8, about 1:6, about 1:4, about 1:3, about 1:2, about 2:3, about 1:1, about 3:2, about 2:1, about 4:1, about 6:1, about 8:1, or about 10:1, and useful ranges may be selected between any of these values (for example, about 1:10 to about 10:1, about 1:8 to about 8:1, about 1:6 to about 6:1, about 1:4 to about 4:1, about 2:3 to about 3:2, about 1:2 to about 2:1, about 1:3 to about 1:1, or about 1:2 to about 2:3). In one embodiment, the weight ratio of [NANL]:[NAL] is about 2:3. In one embodiment, the weight ratio of [NANL]:[NAL] is about 1:2. In one embodiment, the weight ratio of [NANL]:[NAL] is about 2:1.

In various embodiments the weight ratio of [NANL]:[NFL]:[NAL] in the composition or extract is from about 1:12:1, to about 2:5:3, for example from about 1:12:1 to about 1:4:1, or from about 4:12:1 to about 4:5:1, or from about 1:12:4 to about 1:5:4. In one embodiment, the weight ratio of [NANL]:[NFL]:[NAL] is about 2:12:3.

In one embodiment the weight ratio of [NANL]:[NFL]:[NAL] in the composition or extract is about 1:8:2. In another embodiment, the weight ratio of [NANL]:[NFL]:[NAL] in the composition or extract is 2:4:1 or 1:5:1.

In various embodiments NANL comprises about 1%, 3%, 5%, 6%, 7%, 8%, 9%, 10%, 12%, 14% or about 15% by weight of the total loline alkaloids in the composition, and useful ranges may be selected between any of these values (for example, from about 1% to about 15%, about 2% to about 12%, about 5% to about 12%, or from about 5% to about 10% by weight).

In one embodiment, the predominant loline alkaloid in the composition is NFL. In various embodiments NFL comprises about 50%, 55%, 60%, 65%, 70%, 75%, 80%, 85%, or about 90% by weight of the total loline alkaloids in the composition, and useful ranges may be selected between any of these values (for example, from about 50% to about 90%, about 60% to about 85%, about 65% to about 80%, or from about 70% to about 80% by weight).

In various embodiments NAL comprises about 4%, 5%, 7.5%, 10%, 12%, 13%, 14%, 15%, 17.5%, 20%, 25% or about 30% by weight of the total loline alkaloids in the composition, and useful ranges may be selected between any of these values (for example, from about 4% to about 30%, about 5% to about 25%, about 10% to about 25%, or from about 10% to about 20% by weight).

In various embodiments loline comprises about 0.5%, 1%, 1.5%, 2%, 2.5% 3%, 3.5%, 4%, 4.5%, 5%, 6%, 7%, 8%, 9%, or about 10% by weight of the total loline alkaloids in the composition, and useful ranges may be selected between any of these values (for example, from about 0.5% to about 10%, about 0.5% to about 5%, about 1% to about 5%, or from about 1% to about 4% by weight).

In various embodiments the composition comprises about 10, 15, 20, 22.5, 25, 27.5, 30, 35 or about 40 mg/g NANL, and useful ranges may be selected between any of these values (for example, from about 10 to about 40 mg/g, about 15 to about 30 mg/g, about 20 to about 30 mg/g, or from about 20 to about 25 mg/g).

In various embodiments the composition comprises about 100, 110, 120, 130, 140, 150, 160, 170, 180, 185, 190, 195, 200, 205, 210, 220, 230, 240 or about 250 mg/g NFL, and useful ranges may be selected between any of these values (for example, from about 100 to about 250 mg/g, about 150 to about 220 mg/g, about 180 to about 210 mg/g, or from about 185 to about 200 mg/g).

In various embodiments the composition comprises about 10, 15, 20, 25, 30, 35, 40, 45, 50, 55, 60, 65, 70 or about 75 mg/g NAL, and useful ranges may be selected between any of these values (for example, about 10 to about 75 mg/g, about 25 to about 60 mg/g, about 30 to about 50 mg/g, or about 30 to about 45 mg/g).

In various embodiments the composition comprises about 1, 2, 2.5, 3, 3.5, 4, 4.5, 5, 5.5, 6, 7.5, 8, 8.5, 9, 9.5 or about 10 mg/g loline, and useful ranges may be selected between any of these values (for example, from about 1 to about 10 mg/g, about 2.5 to about 10 mg/g, about 4 to about 10 mg/g, or from about 5 to about 8 mg/g).

In one embodiment the composition comprises the one or more loline alkaloids as the sole pesticidal ingredient. In another embodiment the composition comprises the one or more loline alkaloids as the sole insecticidal ingredient. In a further embodiment the composition comprises the one or more loline alkaloids as the sole active ingredient.

In one embodiment the composition comprises N-formylloline as the sole pesticidal ingredient. In another embodiment the composition comprises N-formylloline as the sole insecticidal ingredient. In a further embodiment the composition comprises N-formylloline as the sole active ingredient.

In one embodiment the composition does not comprise flonicamid or thiamethoxam.

In another embodiment, the composition has a molar ratio of total hydroxyl groups to N-formylloline of less than about 20, less than about 18, less than about 16, less than about 14, less than about 12 or less than about 10.

In another embodiment, the composition has a molar ratio of total nitrogen-containing groups to N-formylloline of less than about 20, less than about 18, less than bout 16, less than about 14, less than about 12 or less than about 10.

In various embodiments, the hydroxyl groups are selected from water, an alcohol hydroxyl group, a carboxylic acid hydroxyl group, or mixtures thereof. In certain embodiments, the hydroxyl groups are selected from water, an alcohol hydroxyl group, or mixtures thereof. In certain exemplary embodiments, the hydroxyl groups are selected from an alcohol hydroxyl group.

In another embodiment, the one or more solvents comprise at least about 10, 15, 20, 25, 30, 35, 40, 45, 50, 55, 60, 65, 70, 75, 80, 85, 90, or 99% w/w of the composition, and useful ranges may be selected between any of these values (for example, about 10 to about 99, about 30 to about 99, about 40 to about 99, about 60 to about 99, or about 80 to about 99% w/w).

In various embodiments the one or more solvents may be one or more organic solvents.

In one embodiment the one or more solvents are odourless or substantially odourless, have a low flashpoint, have low flammability, and/or are substantially soluble in water.

In one embodiment the one or more solvents are non-phytotoxic, non-toxic to human and non-human animals, and/or biodegradeable.

In one embodiment the one or more solvents may each have a boiling point greater than about 80° C., for example greater than about 85, 90, 95, 100, 110, 120, 130, 140, 150, or 160° C. In another embodiment the one or more solvents may each have a boiling point greater than about 160° C.

In one embodiment, the one or more solvents are selected from the group comprising alcohols, ketones, esters, ethers, carbonates, amines, amides, nitriles, sulfoxides, and sulfones. In one embodiment, the one or more solvents are selected from the group comprising alcohols, ketones, esters, ethers, carbonates, amides, nitriles, and sulfoxides.

In one embodiment, the one or more solvents may be selected from the group comprising glycols, or ethers or esters thereof. In one embodiment, the one or more solvents may be selected from the group comprising glycols or ethers. In one embodiment, the one or more solvents may be selected from the group comprising glycols.

In one embodiment the glycols or ethers or esters thereof may be polyalkylene glycols, or ethers or esters thereof. In one embodiment, the polyalkylene glycols, or ethers or esters thereof may be of the formula $R^{10}O—[(C_{1-6}alkylene)O]_x—R^1$, wherein $R^1$ and $R^{10}$ are each independently selected from hydrogen, aliphatic, cycloaliphatic, acyl, aryl, or arylaliphatic, and x is an integer from 2 to 140. In some embodiments, $R^{10}$ and $R^1$ are each independently selected from hydrogen, $C_{1-6}$alkyl, acyl, aryl, or arylalkyl, and x is an integer from 2 to 140. In some embodiments, x is an integer from 2 to 10, 2 to 20, 2 to 30, 2 to 40, 2 to 50, 2 to 60, 2 to 70, 2 to 80, 2 to 90, or 2 to 100. In a preferred embodiment, the polyalkylene glycols or ethers or esters thereof are of the formula $HO—[(C_{1-6}alkylene)O]_x—R^1$. In a preferred embodiment, the polyalkylene glycols or ethers or esters thereof are of the formula $HO—[(C_{2-4}alkylene)O]_x—R^1$. In some embodiments the polyalkylene glycols or ethers or esters thereof may be a polyethylene or polypropylene glycol or ether or ester thereof. In a preferred embodiment, the polyalkylene glycol or ether or ester thereof is a polyethylene glycol or ether or ester thereof. Polyethylene glycols and ethers or esters thereof of various molecular weights are contemplated for use as solvents as described herein. For example, polyethylene glycols or ethers or esters thereof having a molecular weight of from 100 to 6000 are contemplated, such as PEG100, PEG200, PEG300, PEG400, PEG500, PEG1000, PEG5000, and PEG6000. In one embodiment the polyethylene glycols or ethers or esters thereof may have a molecular weight of from 100 to 5000, 100 to 1000, 100 to 500, 200 to 1000, or from 200 to 500. In one embodiment the polyalkylene glycol or ether or ester thereof may be a polyethylene glycol monomethyl ether, such as MPEG350 or MPEG550. In one embodiment the polyethylene glycol monomethyl ether has a molecular weight of from 100 to 5000, 100 to 1000, 100 to 700, 200 to 1000, 200 to 700 or from 200 to 600. In one embodiment, the polyalkylene glycol or ether or ester thereof may be dipropylene glycol methyl ether (e.g. DOWANOL™ DPM). In one embodiment the glycols or ethers thereof of may be polyalkylene glycols or ethers thereof. In one embodiment the glycols may be polyalkylene glycols.

In one embodiment the glycols or ethers or esters thereof may be polyalkylene glycols, or ethers or esters thereof of the formula $R^{10}O—[(C_{1-6}alkylene)O]_x—R^1$, wherein $R^{10}$ is selected from hydrogen, $C_{1-6}$alkyl, acyl, aryl and arylalkyl, and $R^1$ is selected from $C_{1-6}$alkyl, and acyl, and x is an integer from 4 to 140. In some embodiments, x is an integer from 4 to 10, 4 to 20, 4 to 30, 4 to 40, 4 to 50, 4 to 60, 4 to 70, 4 to 80, 4 to 90, or 4 to 100. In a preferred embodiment, the polyalkylene glycols or ethers or esters thereof are of the formula $HO—[(C_{1-6}alkylene)O]_x—R^1$. In a preferred embodiment, the polyalkylene glycols or ethers or esters thereof are of the formula $HO—[(C_{2-4}alkylene)O]_x—R^1$. In one embodiment the polyalkylene glycol or ether or ester thereof may be a polyethylene glycol monomethyl ether, such as MPEG350 or MPEG550. In one embodiment the polyalkylene glycol or ether or ester is MPEG550.

In one embodiment the glycols or ethers or esters thereof of may be monoalkylene glycols or ethers or esters thereof. In one embodiment the monoalkylene glycols or ethers or esters thereof may be of the formula $R^{20}O—(C_{1-6}alkylene)O—R^2$, wherein $R^{20}$ and $R^2$ are each independently selected from hydrogen, aliphatic, cycloaliphatic, acyl, aryl, or arylaliphatic. In some embodiments, $R^{20}$ and $R^2$ are each independently selected from hydrogen, $C_{1-6}$alkyl, acyl, aryl or arylalkyl. In a preferred embodiment, the monoalkylene glycol or ether or ester thereof is of the formula $HO—(C_{1-6}alkylene)O—R^2$. In a preferred embodiment, the monoalkylene glycol or ether or ester thereof is of the formula $HO—(C_{2-4}alkylene)O—R^2$. In a further preferred embodiment, the monoalkylene glycol or ether or ester thereof may be an ethylene or propylene glycol or ether or ester thereof, preferably an ethylene glycol or ether or ester thereof. In a preferred embodiment, $R^2$ may be a phenyl or benzyl group. In a preferred embodiment, the monoalkylene glycol or ether or ester thereof may be an ethylene glycol phenyl ether (e.g. DOWANOL™ EPH). In one embodiment the glycols or ethers thereof may be monoalkylene glycols or ethers thereof. In one embodiment the glycols may be monoalkylene glycols.

In one embodiment, the amine has the formula $R^{25}R^{26}R^{27}N$, wherein $R^{25}$, $R^{26}$, and $R^{27}$ are each independently selected from hydrogen or aliphatic, or $R^{26}$ and $R^{27}$ together with the nitrogen atom to which they are attached form a 5 to 8 membered heterocyclyl ring, which may comprise an additional heteroatom. In one embodiment, the amine has the formula $R^{25}R^{26}R^{27}N$, wherein $R^{25}$, $R^{26}$, and $R^{27}$ are each independently selected from hydrogen or $C_{1-6}$alkyl, or $R^{26}$ and $R^{27}$ together with the nitrogen atom to which they are attached form a 5 to 8 membered heterocyclyl ring, which may comprise an additional heteroatom. In some embodiments, $R^{25}$, $R^{26}$, and $R^{27}$ are each independently selected from hydrogen or $C_{1-6}$alkyl. In some embodiments, $R^{25}$ is hydrogen or $C_{1-6}$alkyl, and $R^{26}$ and $R^{27}$ together with the nitrogen atom to which they are attached form a 5 to 8 membered heterocyclyl ring, which may comprise an additional heteroatom.

In one embodiment the amine may be a polyamine, for example a diamine. In one embodiment the amine may be a monoalkylene diamine. In one embodiment the monoalkylene diamine may be of the formula $R^{31}NH—(C_{1-6}$alkylene)$NR^{30}—R^{32}$, wherein $R^{31}$ and $R^{32}$ are each independently selected from hydrogen, aliphatic, cycloaliphatic, acyl, aryl, or arylaliphatic, and $R^{30}$ is selected from hydrogen or aliphatic. In some embodiments, $R^{31}$ and $R^{32}$ are each independently selected from hydrogen, $C_{1-6}$alkyl, aryl or arylalkyl, and $R^{30}$ is selected from hydrogen or $C_{1-6}$alkyl. In a preferred embodiment, the monoalkylene diamine is of the formula $NH_2—(C_{1-6}$alkylene)$NH—R^{32}$. In a preferred embodiment, the monoalkylene diamine is of the formula $NH_2—(C_{2-4}$ alkylene)$NH—R^{32}$.

Suitable amides are described in WO 2007/107745, the entirety of which is incorporated herein by reference. In one embodiment the amide may be of the formula $CH_3CH(OH)C(═O)NR^3R^4$ wherein $R^3$ and $R^4$ are each independently selected from hydrogen, $C_{1-6}$alkyl, $C_{2-6}$alkenyl, or $C_{3-6}$cycloalkyl, each of which is optionally substituted by up to three substituents independently selected from phenyl, hydroxyl, $C_{1-5}$alkoxy, morpholinyl and $NR^5R^6$ where $R^5$ and $R^6$ are each independently selected from $C_{1-3}$alkyl, or phenyl optionally substituted by up to three substituents independently selected from $C_{1-3}$alkyl; or $R^3$ and $R^4$ together with the nitrogen atom to which they are attached form a morpholinyl, pyrrolidinyl, piperidinyl or azepanyl ring, each of which is optionally substituted by up to three substituents each independently selected from $C_{1-3}$alkyl. In some embodiments, $R^3$ and $R^4$ are each independently selected from hydrogen, $C_{1-6}$alkyl, or $C_{2-6}$alkenyl. In further embodiments, $R^3$ and $R^4$ are each independently selected from hydrogen or $C_{1-6}$alkyl. In a preferred embodiment, $R^3$ and $R^4$ are each independently selected from $C_{1-6}$alkyl. In a preferred embodiment, the amide may be dimethyllactamide (DMLA).

In one embodiment the ketone may be of the formula $R^7C(═O)R^8$, wherein $R^7$ and $R^8$ may each independently be selected from aliphatic, cycloaliphatic, aryl, or arylaliphatic. In some embodiments, $R^7$ and $R^8$ are each independently selected from $C_{1-6}$alkyl, aryl, or arylalkyl. In some embodiments, $R^7$ and $R^8$ may each independently be selected from $C_{1-6}$alkyl or aryl. In a preferred embodiment, $R^7$ may be $C_{1-6}$alkyl and $R^8$ may be aryl. In a preferred embodiment, the ketone may be acetophenone.

In one embodiment, the one or more solvents may be an aliphatic alcohol, or ether or ester thereof. In one embodiment the aliphatic alcohol, or ether or ester thereof may be of the formula $R^{40}OR^{41}$, wherein $R^{40}$ may be aliphatic, preferably $C_{1-6}$alkyl, and $R^{41}$ may be hydrogen, aliphatic, preferably $C_{1-6}$alkyl, or acyl.

In one embodiment the alcohol may be a cycloaliphatic alcohol. In one embodiment, the cycloaliphatic alcohol may be a $C_{5-8}$cycloalkyl alcohol. In some embodiments, the cycloaliphatic ring is substituted with from 1 to 3 hydroxyl groups. In some embodiments, the cycloaliphatic alcohol may be a $C_{5-7}$cycloalkyl, preferably a $C_{5-6}$cycloalkyl, substituted with from 1 to 3 hydroxyl groups. In a preferred embodiment, the cycloaliphatic alcohol may be cyclohexanol.

In one embodiment the alcohol may be an aromatic alcohol. In one embodiment the aromatic alcohol may be of the formula arylaliphatic-OH. In some embodiments, the aromatic alcohol is of the formula arylalkyl-OH. In a preferred embodiment, the aromatic alcohol may be benzyl alcohol.

In one embodiment, the one or more solvents may be a triol, or ether, ester, or carbonate thereof. In one embodiment, the one or more solvents may be an alkylene triol or ether, ester, or carbonate thereof, such as a $C_{3-5}$alkylene triol or ether, ester, or carbonate thereof, for example a mono-, di- or tri-ester. In some embodiments, the triol or ether, ester, or carbonate thereof is glycerol or an ether, ester, or carbonate thereof. In some embodiments, the triol or ether, ester, or carbonate thereof has the formula $R^{70}OCH_2CH(OR^{71})CH_2OR^{72}$, wherein $R^{70}$, $R^{71}$, and $R^{72}$ are each independently selected from hydrogen, aliphatic, cycloaliphatic, aryl, arylaliphatic, acyl, or $R^{71}$ and $R^{72}$ together with the oxygens to which they are attached form a 5 membered ring. In some embodiments, $R^{70}$, $R^{71}$, and $R^{72}$ are each independently selected from hydrogen, $C_{1-6}$alkyl, or acyl. In some embodiments, the acyl is of the formula $C_{1-20}C(O)$, for example acetyl. In some embodiments, the carbonate of the triol is a cyclic carbonate. In one embodiment the ether of the triol is an acetal. In some embodiments, $R^{71}$ and $R^{72}$ together with the oxygens to which they are attached form a 5 membered ring. In some embodiments the ether, ester, or carbonate of the triol is an ether, ester, or carbonate of the triol wherein at least one of the hydroxyl groups of the triol is not in the form of an ether, ester, or carbonate (that is, at least one of the hydroxyl groups is a free hydroxyl group). Preferably, at least one of $R^{70}$, $R^{71}$, and $R^{72}$ is hydrogen. In some embodiments, $R^{70}$ is hydrogen. In a preferred embodiment, the one or more solvents is glycerine carbonate.

In one embodiment the ester may be a mono-ester, a di-ester or a tri-ester. In one embodiment the di-ester may be a di-ester of a dicarboxylate. In one embodiment the tri-ester may be a tri-ester of a tricarboxylate. In one embodiment the ester may be an α-hydroxy ester. In one embodiment the mono- or di-ester may be an α-hydroxy ester.

In one embodiment, the mono-ester may be of the formula $R^{77}C(O)OR^{17}$, wherein $R^{77}$ and $R^{17}$ are each independently selected from an aliphatic, cycloaliphatic, aryl, or arylaliphatic group, each of which may be optionally substituted with one or more hydroxyl groups. In one embodiment, $R^{77}$ and $R^{17}$ are each independently selected from $C_{1-12}$alkyl, aryl, or arylalkyl, each of which may be optionally substituted with one or more hydroxyl groups. In a preferred embodiment, $R^{17}$ is a $C_{1-12}$alkyl. In some embodiments, $R^{77}$ is a cycloaliphatic, aryl, or arylaliphatic group, preferably aryl. In a preferred embodiment, the mono-ester may be butyl benzoate. In some embodiments, $R^{77}$ is $C_{1-6}$alkyl, optionally substituted with one or more hydroxyl groups. In one embodiment, the mono-ester is $CH_3CH(OH)C(=O)OR^{17}$. In a preferred embodiment, the mono-ester may be esters of lactate such as methyl lactate, ethyl lactate, n-propyl lactate, n-butyl lactate, or 2-ethylhexyl lactate (marketed under the Purasolv® brand name).

In one embodiment, the di-ester may be of the formula $R^{19}OC(O)C_{1-6}alkylC(O)OR^{18}$, wherein $R^{19}$ and $R^{18}$ are each independently selected from an aliphatic, cycloaliphatic, aryl, or arylaliphatic group. In one embodiment, $R^{19}$ and $R^{18}$ are each independently selected from $C_{1-6}$alkyl, aryl, or arylalkyl. In a preferred embodiment $R^{19}$ and $R^{18}$ are each independently selected from $C_{1-6}$alkyl. In a preferred embodiment, the ester may be di-esters of adipic, glutaric and succinic acids, such as dimethyl succinate, dimethyl adipate and dimethyl glutarate (e.g. Estasol™), In one embodiment, the tri-ester may be of the formula

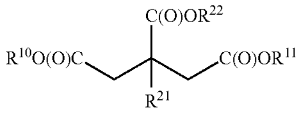

wherein $R^{10}$, $R^{11}$ and $R^{22}$ may each independently be an aliphatic cycloaliphatic, aryl, or arylaliphatic group, and $R^{21}$ may be hydrogen or hydroxyl. In one embodiment, $R^{10}$, $R^{11}$ and $R^{22}$ may each independently be selected from $C_{1-6}$alkyl, aryl, or arylalkyl. In a preferred embodiment, $R^{10}$, $R^{11}$ and $R^{22}$ may each independently be $C_{1-6}$alkyl. In a preferred embodiment, the tri-ester may be triethylcitrate.

In one embodiment the nitrile may have a formula $R^{12}$—CN, wherein $R^{12}$ may be an aliphatic, cycloaliphatic, aryl, or arylaliphatic group. In one embodiment, $R^{12}$ may be a $C_{1-6}$alkyl, aryl, or arylalkyl. In one embodiment, $R^{12}$ may be a $C_{1-6}$alkyl. In a preferred embodiment, the nitrile is acetonitrile.

In one embodiment, the sulfoxide may be of the formula $R^{13}S(O)R^{14}$, wherein $R^{13}$ and $R^{14}$ may each independently be aliphatic, cycloaliphatic, aryl, arylaliphatic. In some embodiments, $R^{13}$ and $R^{14}$ are each independently selected from $C_{1-6}$alkyl, aryl, or arylalkyl. In a preferred embodiment, $R^{13}$ and $R^{14}$ may each independently be $C_{1-6}$alkyl. In a preferred embodiment, the sulfoxide may be dimethylsulfoxide.

In one embodiment, the sulfone may be of the formula $R^{15}SO_2R^{16}$, wherein $R^{15}$ and $R^{16}$ may each independently be an aliphatic, cycloaliphatic, aryl or arylaliphatic group. In some embodiments, $R^{15}$ and $R^{16}$ are each independently selected from $C_{1-6}$alkyl, aryl, or arylalkyl. In a preferred embodiment, $R^{15}$ and $R^{16}$ may each independently be $C_{1-6}$alkyl.

In one embodiment, the one or more solvents are selected from the group comprising a) polyalkylene glycols, or ethers or esters thereof, for example polyalkylene glycols, or ethers or esters thereof, of the formula $R^{10}O—[(C_{1-6}alkylene)O]_x—R^1$, b) monoalkylene glycols, or ethers or esters thereof, for example, monoalkylene glycols, or ethers or esters thereof of the formula $R^{20}O—(C_{1-6}alkylene)O—R^2$, c) amines of the formula $R^{25}R^{26}R^{27}N$, d) monoalkylene diamines, for example monoalkylene diamines of the formula $R^{31}NH—(C_{1-6}alkylene)NR^{30}—R^{32}$, e) amides of the formula $CH_3CH(OH)C(=O)NR^3R^4$ f) ketones, for example ketones of the formula $R^7C(=O)R^8$, g) aliphatic alcohols, for example aliphatic alcohols of the formula $R^{40}OR^{41}$, h) cycloaliphatic alcohols, i) aromatic alcohols, j) triols or ethers, esters, or carbonates thereof, for example triols or ethers, esters, or carbonates thereof, of the formula $R^{70}OCH_2CH(OR^{71})CH_2OR^{72}$ k) mono-esters, for example mono-esters of the formula $R^{77}C(O)OR^{17}$, l) di-esters, for example di-esters of the formula $R^{19}OC(O)C_{1-6}alkylC(O)OR^{18}$, m) tri-esters, for example tri-esters of the formula

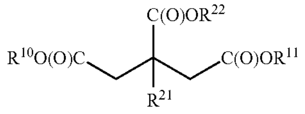

n) nitriles, for example nitriles of the formula $R^{12}$—CN, o) sulfoxides, for example, sulfoxides of the formula $R^{13}S(O)R^{14}$, p) sulfones, for example, sulfones of the formula $R^{15}SO_2R^{16}$, or q) any two or more of a) to p) above, wherein each of the variables in the formulae above are used as defined in any of the embodiments defined herein.

In various embodiments the one or more solvents may be selected from the group comprising dimethyllactamide, dipropylene glycol methyl ether, ethylene glycol phenyl ether, acetophenone, cyclohexanol, polyethylene glycol, polyethylene glycol methyl ether, dimethylsuccinate, dimethylglutarate, dimethyl adapate, butyl benzoate, triethylcitrate, glycerol, glycerine carbonate, ethylene glycol, propylene glycol, dimethyl sulfoxide, benzyl alcohol, and acetonitrile, or any combination of any two or more thereof.

In various embodiments the one or more solvents may be selected from the group comprising dimethyllactamide, dipropylene glycol methyl ether, ethylene glycol phenyl ether, acetophenone, cyclohexanol, polyethylene glycol, polyethylene glycol methyl ether, dimethylsuccinate, dimethylglutarate, dimethyl adapate, butyl benzoate, triethylcitrate, glycerol, glycerine carbonate, ethylene glycol, propylene glycol, dimethyl sulfoxide, benzyl alcohol, 2-ethylhexyl lactate and acetonitrile, or any combination of any two or more thereof.

In various embodiments the one or more solvents may be selected from the group comprising dimethyllactamide, dipropylene glycol methyl ether, ethylene glycol phenyl ether, acetophenone, cyclohexanol, polyethylene glycol, polyethylene glycol methyl ether, dimethylsuccinate, dimethylglutarate, dimethyl adapate, butyl benzoate, triethylcitrate, glycerine carbonate, ethylene glycol, propylene glycol, 2-ethylhexyl lactate and benzyl alcohol, or any combination of any two or more thereof.

In various embodiments the one or more solvents may be selected from the group comprising dimethyllactamide, ethylene glycol phenyl ether, polyethylene glycol having a molecular weight of from 100 to 6000, a polyethylene glycol methyl ether having a molecular weight of from 100 to 1000, dimethylsuccinate, dimethylglutarate, dimethyl adapate, butyl benzoate, triethylcitrate, glycerine carbonate, 2-ethylhexyl lactate and benzyl alcohol, or any combination of any two or more thereof.

Unless indicated otherwise, the chemical groups referred to herein may be optionally substituted. As used herein, the term "substituted" is intended to mean that one or more hydrogen atoms in the group indicated is replaced with one or more independently selected suitable substituents, provided that the normal valency of each atom to which the substituent/s are attached is not exceeded, and that the substitution results in a stable compound. The term "stable" as used herein in this context refers to compounds which possess stability sufficient to allow manufacture and which maintain their integrity for a period of time sufficient to be useful for the purposes described herein. Examples of suitable optional substituents, for example, for the aliphatic, cycloaliphatic, alkyl, alkenyl, cycloalkyl, aryl, alkylene, arylaliphatic, arylalkyl, alkoxy groups in the compounds described herein, include but are not limited to halo, CN, $NO_2$, $NR^aR^b$, $C_{1-6}$haloalkyl, $C_{1-6}$haloalkoxy, $C(O)OR^a$, $C(O)NH_2$, $C(O)NHR^a$, $C(O)NR^aR^b$, $SO_2R^a$, $OR^a$, $SR^a$, $S(O)R^a$, $C(O)R^a$, and $C_{1-6}$alkyl; wherein $R^a$ and $R^b$ are each independently $C_{1-6}$alkyl. In certain embodiments, suitable optional substituents include but are not limited to halo, CN, $NO_2$, $C_{1-6}$haloalkyl, $C_{1-6}$haloalkoxy, $OR^a$, $SR^a$, and $C_{1-6}$alkyl. In certain embodiments, the suitable optional substituents include but are not limited to $C_{1-6}$alkyl.

In another embodiment, the one or more solvents comprise, consist essentially of, or consist of hydroxyl and nitrogen-containing groups having a nucleophilicity coefficient of less than about 0.5 eV, less than about 0.4 eV, less than about 0.35 eV, less than about 0.3 eV, or less than about 0.28 eV.

In various embodiments the one or more solvents are aprotic or comprise one or more nucleophilic groups, the nucleophilicity coefficient of each nucleophilic group being less than about 0.4 eV, less than about 0.35 eV, less than about 0.3 eV, or less than about 0.28 eV. By way of example, in an embodiment where the nucleophilicity coefficient of each nucleophilic group is less than about 0.4 eV, the one or more solvents will not contain any nucleophilic group with a higher nucleophilicity coefficient.

In one embodiment, the one or more solvents comprise a solvent system that is substantially non-aqueous. In a further embodiment, the one or more solvents comprise a solvent system that contains less than 5% w/w water. In various embodiments, the one or more solvents comprise a solvent system that contains less than 4%, less than 3%, less than 2%, or less than 1% w/w water. In a further embodiment, the one or more solvents comprise a solvent system that is non-aqueous.

It should be appreciated that stable formulations as described herein are achieved by balancing OH equivalence of the one or more solvent and water content of the composition to achieve a stable formulation with a low overall molar ratio of total OH to NFL. For example, a higher water content may be tolerated if the OH equivalence of the solvent system (and/or eV) is low. Conversely, in embodiments where less water is present—for example, in the loline alkaloid-providing ingredient prior to formulation—a solvent with a higher OH equivalence and/or eV can be tolerated and still provide a stable formulation.

It will also be appreciated that in embodiments where less water is present, the use of solvents or a mixture of solvents (potentially including solvents that have high OH equivalence when used (alone) in high quantities) while still having a sufficiently low overall molar ratio of total OH to NFL is enabled, whereby such formulations can benefit from useful properties of solvents that would otherwise lead to unacceptable NFL degradation.

Further, in certain embodiments a higher overall molar ratio of total OH and/or nitrogen-containing groups to NFL can be tolerated when the nucleophilicity coefficient is lower.

In one embodiment the composition is substantially non-aqueous. In a further embodiment, the composition comprises less than 5% w/w water. In various embodiments, the composition comprises less than 4%, less than 3%, less than 2%, or less than 1% w/w water. In a further embodiment, the composition is non-aqueous.

In another embodiment, the composition is substantially non-aqueous prior to formulation or dilution for application.

In one embodiment, the composition further comprises one or more of the following: a water scavenger, a surfactant, a preservative, a desiccant, or a buffering agent.

In one embodiment the composition further comprises a surfactant. In various embodiments the surfactant is selected from the group comprising non-ionic surfactants, ionic surfactants, anionic surfactants, cationic surfactants and/or amphoteric surfactants. In various embodiments the surfactant comprises a sulphate, for example, an alkyl sulphate or an alkyl ether sulphate, a sulphonate, for example, an alkylbenzene sulphonate or a linear alkylbenzene sulphonate (LAB) such as calcium dodecylbenzene sulphonate, a phosphate ester, for example, a phosphate monoester or a mixed phosphate diester, an alkyl ether carboxylate, for example, a laureth carboxylate, an alkyl quaternary surfactant, for example, a monoalkyl quaternary ammonium surfactant, an ester quat or an alkyl betaine. In various embodiments the surfactant comprises ammonium lauryl sulphate, sodium lauryl sulphate, sodium laureth sulphate or sodium myreth sulphate, sodium dioctyl sulphosuccinate, sodium bistridecyl sulphosuccinate, sodium dihexyl sulphosuccinate, sodium dicyclohexyl sulphosuccinate, sodium diamyl sulphosuccinate, sodium dicyclohexyl sulphosuccinate, sodium diisobutyl sulphosuccinate, perfluorooctanesulphonate (PFOS), perfluorobutanesulphonate or sodium stearate, or a combination of any two or more thereof.

Combinations of any two or more solvents, and combinations of any two or more surfactants, including of those recited above, are also contemplated.

In one embodiment the solvent(s) and/or surfactant(s) are substantially free of hydroxyl groups and nitrogen-containing groups. In one embodiment the solvent(s) and/or surfactant(s) comprise no hydroxyl groups or nitrogen-containing groups.

In one embodiment the composition is substantially free of solvents comprising hydroxyl groups and nitrogen-containing groups, surfactants comprising hydroxyl groups and nitrogen-containing groups, and/or other compounds comprising hydroxyl groups and nitrogen-containing groups. In one embodiment the composition comprises no solvents comprising hydroxyl groups or nitrogen-containing groups, surfactants comprising hydroxyl groups or nitrogen-containing groups, and/or other compounds comprising hydroxyl groups or nitrogen-containing groups.

In one embodiment the composition is substantially free of hydroxyl groups and nitrogen-containing groups. In another embodiment the composition comprises no hydroxyl groups or nitrogen-containing groups.

In various embodiments the molar amount of hydroxyl groups and/or and nitrogen-containing groups in the solvent(s) comprising one or more hydroxyl groups and/or and nitrogen-containing groups, and/or surfactant(s) comprising one or more hydroxyl groups and/or and nitrogen-containing groups is less than about 50%, 40%, 30%, 20%, 10%, 7.5%, 5%, 4%, 3%, 2%, 1% or about 0.5% of the molar amount of N-formylloline (NFL) in the composition. It will be appreciated that the composition above generally is a composition, for example a concentrate composition, which has not yet been diluted by a carrier or adjuvant for application.

In one embodiment the composition further comprises a preservative. Suitable preservatives for use in the composition are known in the art.

In one embodiment the surfactant has insecticidal activity. In one embodiment the surfactant is non-phytotoxic, non-toxic to humans and non-human animals and/or biodegradeable. In one embodiment the surfactant is substantially soluble in polar and non-polar solvents.

In various embodiments the composition comprises about 1, 2, 3, 4, 5, 6, 7, 8, 9, 10, 12, 15, 20, 25, 30, 35, 40, 45 or about 50 by weight of surfactant. Useful ranges may be selected between any of these values (for example, from about 1 to about 50, about 1 to about 20, about 1 to about 10, or from about 2% to about 8%).

In various embodiments the composition comprises about 0.01, 0.05, 0.075, 0.1, 0.125, 0.15, 0.175, 0.2, 0.225, 0.25, 0.275, 0.3, 0.4, 0.5, 0.6, 0.7, 0.8, 0.9 or about 1% by weight of preservative, and useful ranges may be selected between any of these values (for example, from about 0.01% to about 1%, about 0.05% to about 0.5%, about 0.05% to about 0.4%, or from about 0.1% to about 0.3%).

In one embodiment the composition further comprises an antioxidant. In one embodiment the antioxidant is a lipid-soluble antioxidant. In various embodiments the antioxidant comprises one or more tocopherols or tocotrienols, for example, vitamin E, propyl gallate, hydroquinones, for example, tert-butylhydroquinone, phenols, for example, butylated hydroxyanisole or butylated hydroxytoluene, carotenoids, for example, β-carotene, α-carotene, β-cryptoxanthin, lutein, lycopene and zeaxanthin, or a combination of any two or more thereof.

In various embodiments the composition comprises at least about 100, 110, 120, 130, 140, 150, 160, 170, 180, 185, 190, 195, 200, 205, 210, 220, 230, 240 or about 250 mg/g NFL, after about 1, 2, 3, or 4 weeks or about 1, 2, 3, 4, 6, 9, 12, 18, 24, 36 or 48 months storage at a temperature of about −20, 4, 10, 15, 20, 25, 30, 35, 40, 45, 50, 54, 55, or about 60° C., or at ambient temperature. For example, preferably the composition comprises at least about 180 mg/g NFL after storage for 2 weeks at a temperature of about −20° C., 4° C. or about 54° C.

In various embodiments the composition retains at least about 50, 60, 70, 75, 80, 85, 90, 95, 98, 99 or about 100% NFL after about 1, 2, 3, or 4 weeks or about 1, 2, 3, 4, 6, 9, 12, 18, 24, 36 or 48 months storage at a temperature of about −20, 4, 10, 15, 20, 25, 30, 35, 40, 45, 50, 54, 55, or about 60° C., or at ambient temperature. For example, preferably the composition comprises at least about 80% NFL after storage for 2 weeks at a temperature of about −20° C., 4° C. or about 54° C.

In various embodiments less than about 50%, 60%, 70%, 75%, 80%, 85%, 90%, 95%, 98%, 99% or about 100% of the NFL in the composition is degraded or hydrolysed after about 1, 2, 3, or 4 weeks or about 1, 2, 3, 4, 6, 9, 12, 18, 24, 36 or 48 months storage at a temperature of about −20, 4, 10, 15, 20, 25, 30, 35, 40, 45, 50, 54, 55, or about 60° C., or at ambient temperature. For example, preferably less than about 20% of the NFL in the composition is degraded or hydrolysed after storage for 2 weeks at a temperature of about −20° C., 4° C. or about 54° C.

In another aspect the invention provides a method of producing a composition useful herein, comprising the step of admixing one or more loline alkaloids with one or more solvents to form the composition, wherein the composition is substantially free of solvents comprising hydroxyl groups and/or nitrogen-containing groups.

In one embodiment, the method of producing a composition of the present invention comprises the steps of:

a) providing N-formylloline (NFL) and optionally one or more further loline alkaloids of formula (I), and
b) combining the loline alkaloids with one or more solvents to form a composition;

wherein the molar ratio of total hydroxyl and nitrogen-containing groups to N-formylloline of the composition is equal to or less than about 20.

In one embodiment the composition is in the form of a concentrate that is diluted before application. In one embodiment the composition is admixed with water before application.

In one embodiment, the composition is admixed with water to a final concentration of loline alkaloids of about 2, 2.5, 5, 7.5, 10, 15, 20, 25, 30, 35, 40, 45, 50, 75, 100, 125, 150, 175, or about 200 g per 100 L prior to application.

In various embodiments, the composition is admixed with water and applied at a rate of at least about 100, 150, 200, 250, 300, 350, 400, 450, or 500 L/Ha.

In one embodiment, the composition is admixed with a composition comprising one or more antioxidants described above before application. In various embodiments, the composition for application comprises about 0.25, 0.5, 0.75, 1, 1.25, 1.5, 1.75, 2, 2.25, 2.5, 2.75, 3, 3.5, 4, 4.5, 5, 6, 7, 8, 9, 10, 12, 15, 18, 20, 25, 30, 35, 40 or about 50 mL of the antioxidant, for example, vitamin E, per litre, and useful ranges may be selected between any of these values (for example, about 0.25 to about 50 mL/L, about 0.5 to about 10 mL/L, about 0.5 to about 5 mL/L, or about 1 to about 5 mL/L).

In one embodiment, a desiccation protection agent, such as Deep Fried™ Fortune™, or Fortune Plus™, is admixed to a final concentration of about 1 ml/L prior to application.

In another aspect, the invention provides a method of conferring a systemic insect pest resistance to a plant, comprising the step a) providing a composition according to the present invention,
b) topically applying the composition to the plant, thereby to provide uptake of the one or more loline alkaloids by the plant to confer systemic pest resistance.

In another aspect, the invention provides a method for controlling one or more insect pests, comprising the step of applying to a plant or its surroundings or a locus at which insect pests are present a composition as described herein.

In another aspect the invention provides a method of producing a composition for application to a plant or its surroundings, the method comprising the steps of providing a composition as described herein comprising one or more loline alkaloids, and optionally diluting the composition prior to application.

In a further aspect the invention relates to a method of providing one or more loline alkaloids to the systemic circulation of a plant, the method comprising:

providing a composition as described herein comprising one or more loline alkaloids, topically applying the composition to the plant to provide uptake of the one or more loline alkaloids to the systemic circulation of the plant.

In another aspect, the invention relates to a method of conferring systemic insect pest resistance to a plant, the method comprising:

providing a composition as described herein comprising one or more loline alkaloids, for example, one or more substantially pure loline alkaloids derived from a non-synthetic source, topically applying the composition to the plant, thereby to provide uptake of the one or more loline alkaloids by the plant to confer systemic insect pest resistance.

In one embodiment, topical application of the composition provides a systemic concentration of loline alkaloids of at least about 1.0 μg loline alkaloids per g plant. In various embodiments, topical application of the composition provides a systemic concentration of loline alkaloids of at least about 5, 10, 15, 20, 25, 30 40, 50 or 60 μg loline alkaloids per g plant, or more than about 60 μg loline alkaloids per g plant.

In one embodiment, topical application of the composition provides a concentration of loline alkaloids in the stems and/or leaves of the plant of at least about 1.0 μg loline alkaloids per g plant. In various embodiments, topical application of the composition provides a concentration of loline alkaloids in the stems and/or leaves of the plant of at least about 5, 10, 15, 20, 25, 30 40, 50 or 60 μg loline alkaloids per g plant, or more than about 60 μg loline alkaloids per g plant.

In one embodiment, topical application of the composition provides a systemic concentration of loline alkaloids of at least about 20 ppm. For example, topical application of the composition provides a systemic concentration of loline alkaloids of at least about 25, 30, 35 or at least about 40 ppm.

In one embodiment, topical application of the composition provides at least about 20 ppm loline alkaloids in the stems and/or leaves of the plant. In one embodiment, topical application of the composition provides at least about 25, 30, 35 or at least about 40 ppm loline alkaloids in the stems and/or leaves of the plant.

The invention further relates to methods of using the composition for the control of pests, particularly plant and human or non-human animal pests, such as insects, nematodes, and herbivores.

For example, methods of controlling a pest population are also provided by the invention. The method generally involves contacting the population with a pesticidally-effective amount of a composition as described herein. Such methods may be used to kill or reduce the numbers of target pests in a given area, or may be prophylactically applied to a locus, such as an environmental area, to prevent infestation by a susceptible pest.

The invention further relates to the use of a composition of the invention for the control of one or more pests, including one or more insect or nematode pests, such as one or more insect pests, for example, one or more insects or nematodes or one or more insect or nematode pests of one or more animal species.

In one embodiment, the present invention provides a method of controlling one or more insects, including one or more insect pests, for example, one or more insect pests of one or more animal species, the method comprising contacting the one or more insects with a composition of the invention.

The use of a composition produced by a method of the invention in the manufacture of a formulation for the control of one or more pests is similarly contemplated.

The use of a composition produced by a method of the invention or a composition of the invention in the manufacture of a medicament for treating or preventing a pest or parasitic infection in a subject is similarly contemplated.

The present invention further relates to a method for controlling one or more pests, such as one or more insects including one or more parasitic insects, the method comprising applying to a locus, such as a plant or its surroundings, a composition of the invention. The method may also comprise administering a composition of the invention to a subject in need thereof, for example a subject infected by a parasitic or pathogenic insect pest.

In another aspect, the present invention provides a method of reversing, wholly or in part, the resistance of a pest to one or more pesticides or one or more pathogenic agents, the method comprising contacting the insect with a composition of the invention.

Optionally, the method comprises contacting the pest with a composition of the invention together with one or more pesticides or one or more pathogenic agents, or any combination thereof.

In various embodiments, the one or more pesticides or one or more pathogenic agents administered is the same as that to which the pest is or is predicted to be or has become resistant.

In a further aspect, the invention provides a method of controlling one or more pests which have been contacted with a composition of the invention with an amount of a pesticide or a pathogenic agent effective to control said one or more pests.

The one or more pesticides or one or more pathogenic agents may be administered prior to, concurrently with, or after administration of the composition of the invention. Accordingly, administration of the one or more compositions of the invention and the one or more pesticides or one or more pathogenic agents may be simultaneous, sequential, or separate.

In another aspect the invention relates to a method of enhancing the growth or reproduction of a plant, the method comprising contacting the plant with a composition of the invention.

In one embodiment, the method enhances the growth or reproduction of a plant without significant phytotoxicity or symptoms of phytotoxicity.

In one embodiment, the plant is in the presence of a biotic or abiotic stress.

In one embodiment, the abiotic stress is selected from the group consisting of water deficiency, nutrient deficiency, heat stress, salt toxicity, mineral or metal toxicity, and freezing temperatures.

In one embodiment, the biotic stress is selected from the group consisting of insect infestation, nematode infestation, and herbivore grazing. In one embodiment the biotic stress is a stress caused by at least one organism selected from the group consisting of an insect, a nematode, and an herbivore.

In various embodiments, the compositions of the invention are applied prophylactically, for example before the locus, such as a plant, is infected by or exposed to the pest population, such as an insect or insect population. In other embodiments, the composition is applied when infection is established or the pathogen is present, for example when a locus such as a plant is infected by or exposed to an insect, or when an insect is present on or in the locus.

In one embodiment, compositions of the invention are applied directly to the locus, for example are applied directly to a plant or its surroundings. For example, a composition of the invention is admixed with a solvent or emulsified and applied as described herein. In other embodiments, the compositions of the invention are applied indirectly to the locus, such as for example by application to a substrate that is subsequently applied to the locus. In one embodiment the composition is applied to the locus using an irrigation system or chemigation system, for example in hydroponic growth systems.

In one embodiment compositions of the invention are applied to a locus, for example a glasshouse or polytunnel, before planting.

In various embodiments the composition is applied at a rate of at least about 25, 50, 100, 150, 200, 250, 300, 350, 400, 500, 550, 600, 650, 700, 750 or at least about 1000 g lolines/hectare. Generally, application rates of about 100 g to about 500 g lolines/hectare are targeted.

In various embodiments the concentration of loline alkaloids in the leaves of plants treated using a method of the invention is at least 1, 2, 3, 4, 5, 10, 15, 20, 25, 30, 40, 50, 75 or 100 fold greater than the concentration of loline alkaloids in the leaves of untreated plants.

In various embodiments the concentration of loline alkaloids in the stems of plants treated using a method of the invention is at least 1, 1.5, 2, 2.5, 3, 3.5, 4, 4.5, 5, 10, 15, 20, or 25 fold greater than the concentration of loline alkaloids in the stems of untreated plants.

In one embodiment the composition is or is formulated in a seed coating to provide coated seeds, or in plant propagation material.

In various embodiments the coated seeds comprises about 1, 2.5, 5, 7.5, 10, 12.5, 15, 20, 25, 30, 40, 50, 60, 70, 75, 80, 90, 100, 120, 140, 150, 160, 180 or about 200 mg of one or more loline alkaloids per gram of seeds, and useful ranges may be selected between any of these values (for example, from about 1 to about 200 mg, about 10 to about 150 mg, about 10 to about 120 mg, or from about 20 to about 120 mg per gram seeds).

In various embodiments the seed coating comprises a composition of the invention and one or more encapsulation agents selected from the group comprising a polysaccharide such as a gum, for example, xanthan gum, acacia gum, gellan gum, gum arabic, locust bean gum or guar gum, a carageenan (such as carageenan iota, carageenan kappa or carageenan lambda) or a pectin, a water-soluble polymer, such as a hydroxypropyl methylcellulose or a carboxymethylcellulose salt (for example, carboxymethylcellulose sodium salt) or a polyethylene oxide.

In one embodiment the seed coating comprises a composition of the invention and one or more absorptive powders, for example, diatomaceous earth, or adhesives, for example, polyvinylpyrrolidone or polyethylene glycol.

In agricultural and horticultural applications, the invention is applicable to any plant or its surroundings. Illustrative plants are monocotyledonous or dicotyledonous plants such as alfalfa, barley, canola, corn (maize), cotton, flax, kapok, peanut, potato, oat, rice, rye, sorghum, soybean, sugarbeet, sugarcane, sunflower, tobacco, tomato, wheat, turf grass, pasture grass, berry, fruit, legume, vegetable, for example, capsicum, a cucurbit such as cucumber, onion, ornamental plants, shrubs, cactuses, succulents, and trees.

In further illustrative embodiments, the plant may be any plant, including plants selected from the order Solanales, including plants from the following families: Convolvulaceae, Hydroleaceae, Montiniaceae, Solanaceae, and Sphenocleaceae, and plants from the order Asparagales, including plants from the following families: Amaryllidaceae, Asparagaceae, Asteliaceae, Blandfordiaceae, Boryaceae, Doryanthaceae, Hypoxidaceae, Iridaceae, Ixioliriaceae, Lanariaceae, Orchidaceae, Tecophilaeaceae, Xanthorrhoeaceae, and Xeronemataceae.

In another aspect the invention relates to a plant or part thereof treated with, or to which has been applied, a composition of the invention.

In one embodiment the plant or part thereof is reproductively viable, for example, a seed, bulb or cutting or other plant part capable of propagation.

In another aspect the invention relates to a method of treating or preventing a pest, parasite or insect infection or infestation in a subject in need thereof, wherein the subject is a human or non-human animal subject, the method comprising administering to the subject a therapeutically effective amount of a composition of the invention.

In another aspect the invention relates to use of a composition of the invention in the preparation of a composition or medicament for use in any of the methods described herein, for example, for use in treating or preventing a pest, parasite or insect infection or infestation.

In another aspect, the composition is administered topically, orally or parenterally.

In another aspect the invention provides a pharmaceutical or veterinary formulation comprising a composition of the invention and one or more pharmaceutically or veterinarially acceptable excipients, carriers, or diluents.

In one embodiment the method is for treating or preventing an ectoparasite infection or infestation, for example infection or infestation by bedbugs, fleas, flies, gnats, ticks, lice, such as head lice, or mites.

In one embodiment the invention provides a method for treating or preventing an endoparasite infection or infestation, for example infection or infestation by protozoan parasites or parasitic worms, such as helminths.

In one embodiment the composition is administered in the form of a shampoo, collar, cream, gel, drench, pour-on or spot-on formulation, suspension, lotion, ointment, dressing, skin patch, tablet, capsule, bolus, elixir, or injectable.

In various embodiments the composition is applied in an amount sufficient to deliver at least about 5, 10, 20, 25, 30, 40, 45, 50, 55, 60, 70, 75, 80, 90 or at least about 100 μg loline alkaloids per $cm^2$ skin, and useful ranges may be selected between any of these values (for example, about 5 μg to about 100 μg loline alkaloids, about 25 μg to about 100 μg, about 50 μg to about 100 μg, about 25 μg to about 75 μg, or about 50 μg to about 100 μg loline alkaloids per $cm^2$ skin).

In various embodiments the concentration of loline alkaloids in the pharmaceutical or veterinary formulation, for example, for topical application, is at least about 5 μg per mL, 10 μg, 20 μg, 25 μg, 30 μg, 40 μg, 45 μg, 50 μg, 55 μg, 60 μg, 70 μg, 75 μg, 80 μg, 90 μg, 100 μg, 125 μg, 150 μg, 175 μg or at least about 200 μg per mL and useful ranges may be selected between any of these values (for example, about 50 μg to about 200 μg per mL, about 50 μg to about 100 μg, about 75 μg to about 200 μg, about 75 μg to about 100 μg, or about 100 μg to about 200 μg per mL).

In pharmaceutical or veterinarian applications, the invention is applicable to human subjects or any non-human animal subjects, for example, agricultural animals such as cows, sheep, pigs, deer, and goats; companion animals, such as dogs, cats, mice, rats, rabbits, and guinea pigs and horses and birds, such as ostriches, emus, hens, geese, turkeys, and ducks; and fresh- or salt-water fish.

Other aspects of the invention may become apparent from the following description which is given by way of example only and with reference to the accompanying drawings.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It is also intended that where the term "about" is used, for example with reference to a figure, concentration, amount, integer or value, the exact figure, concentration, amount, integer or value is also specifically contemplated.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The invention will now be described by way of example only and with reference to the following drawings.

DETAILED DESCRIPTION OF THE INVENTION

Figure 1:
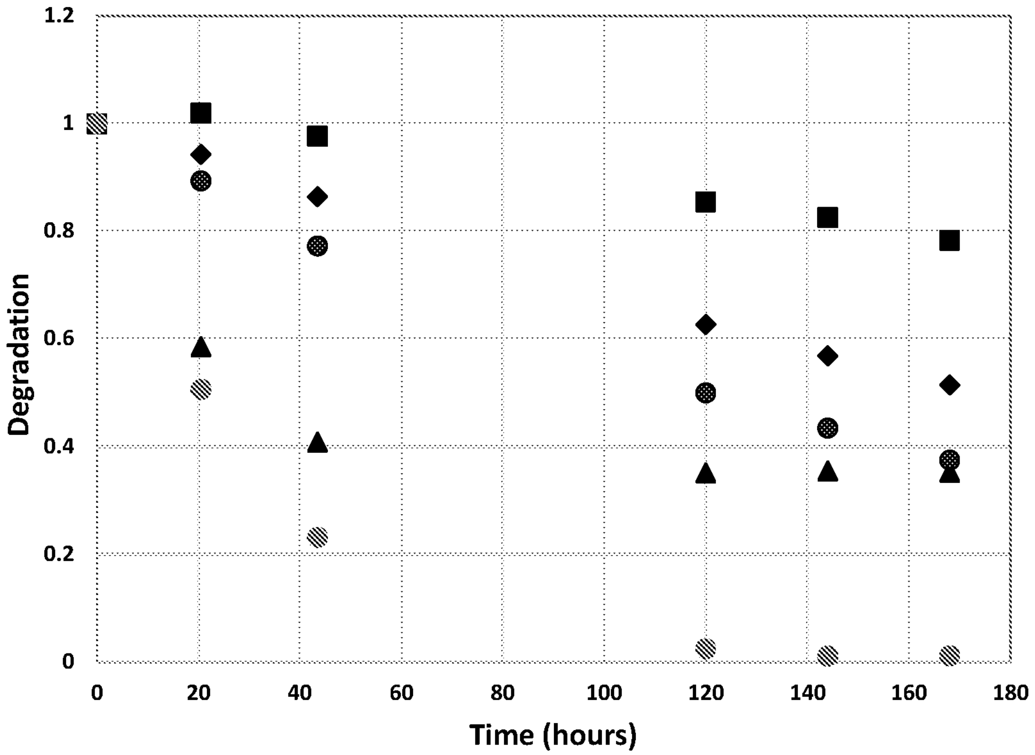
FIGS. 1 and 2 show the percentage degradation of NFL to Loline as a function of time, pH & buffer type at temperatures of 70° C. and 50° C., respectively. Results are depicted for the following buffers: citric acid monohydrate/sodium phosphate dibasic pH 2.6 (triangles), citric acid monohydrate/trisodium citrate dehydrate pH 4 (diamonds), sodium acetate trihydrate/acetic acid pH 4 (squares), sodium phosphate dibasic dehydrate/sodium phosphate monobasic monohydrate pH 6 (black circles), and sodium bicarbonate/sodium carbonate decahydrate pH 10 (grey circles).

The present invention is in part directed to compositions comprising loline alkaloids. The invention is also directed to the use of the compositions of the invention, for controlling pests and pest populations, enhancing plant growth or reproduction, and treating or preventing pest, insect and/or parasitic infections or infestations in humans or non-human animals.

1. Definitions

The term "and/or" can mean "and" or "or".

The term "about," as used herein when referring to a measurable value such as a concentration, molar amount or ratio, dosage, an amount or a time period and the like, is meant to encompass variations of ±20%, ±10%, ±5%, ±1%, ±0.5%, or even ±0.1% of the specified value (e.g., an amount of one or more loline alkaloid, the ratio of one component to another component in a composition, and the like).

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

The term "control" or "controlling" as used herein generally comprehends preventing an increase in, reducing, or eradicating [one or more members of] a population, or preventing, reducing or eradicating infection or infestation by one or more pests or pathogens, such as infection by one or more phytopathogens or pests or insects that infect humans or non-human animals, or inhibiting the rate and extent of such infection, such as reducing a pest population at a locus, for example in or on a plant or its surroundings, or treating or preventing a pest or insect infection or infestation in a human or non-human animal, wherein such prevention or reduction in the infection(s) or population(s) is statistically significant with respect to untreated infection(s) or population(s). Curative treatment is also contemplated. Preferably, such control is achieved by increased mortality amongst the pest or pathogen population.

It will be appreciated that control may be via antagonism, which may take a number of forms. In one form, the compositions of the invention may simply act as a repellent. In another form, the compositions of the invention may render the environment unfavourable for the pest or pathogen. In a further, preferred form, the composition of the invention may incapacitate, render infertile, impede the growth of, impede the spread or distribution of, and/or kill the pest or pathogen. Accordingly, the antagonistic mechanisms include but are not limited to antibiosis, immobilisation, infertility, and toxicity. Therefore, compositions which act as antagonists of one or more pests can be said to have pesticidal activity. For example, compositions that act as antagonists of one or more insects can be said to have insecticidal efficacy. Furthermore, an agent or composition that is or comprises an antagonist of a pest can be said to be an pesticidal agent or a pesticidal composition, for example, an agent that is an antagonist of an insect, including an insect pest of an animal or plant, can be said to be an insecticidal agent. Likewise, a composition that is or comprises an antagonist of an insect, including an insect pest of an animal or plant, can be said to be an insecticidal composition.

Accordingly, as used herein a "pesticidal composition" is a composition which comprises or includes at least one agent that has pesticidal efficacy.

In various embodiments, said pesticidal efficacy is the ability to repel, incapacitate, render infertile, impede the growth of, or kill one or more pests, including insects, nematodes, and herbivores, preferably within 14 days of contact with the insect, more preferably within 7 days, more preferably still the ability to kill one or more insect pests of plants within 7 days.

Accordingly, as used herein an "insecticidal composition" is a composition which comprises or includes at least one agent that has insecticidal efficacy.

The term "functional variant" as used herein in reference to one or more loline alkaloids, for example in respect of one or more loline alkaloids, refers to a loline alkaloid different from the specifically identified entity, for example wherein one or more groups is deleted, substituted, or added, but which possesses at least in part one or more of the biological activities of the specifically-identified entity, such as an ability to elicit one or more biological effects elicited by the specifically-identified loline alkaloid.

In the present case, the functional variant will preferably retain at least a portion of the pesticidal activity of the specifically-identified loline alkaloid or composition of the invention.

Methods and assays to determine one or more biological effects elicited by the loline alkaloids of the invention, such as insecticidal efficacy, are well known in the art, and such methods and assays can be used to identify or verify one or more functional variants of one or more of the loline alkaloids of the invention. For example, an assay of the ability of a loline alkaloid or composition of the invention to kill or otherwise antagonise the growth of a target pest, such as those described herein in the Examples, is amenable to identifying one or more functional variants of the loline alkaloids or compositions of the invention.

The term "plant" as used herein encompasses not only whole plants, but extends to plant parts, cuttings as well as plant products including roots, leaves, flowers, seeds, stems, callus tissue, nuts and fruit, bulbs, tubers, corms, grains, cuttings, root stock, or scions, and includes any plant material whether pre-planting, during growth, and at or post harvest. Plants that may benefit from the application of the present invention cover a broad range of agricultural and horticultural crops. The compositions of the present invention are also especially suitable for application in organic production systems.

When used in respect of a pesticidal agent, such as a pesticidal composition of the invention, the phrase "retaining pesticidal efficacy" and grammatical equivalents and derivatives thereof is intended to mean that the agent still has useful pesticidal activity. Preferably, the retained activity is at least about 35, 40, 45, 50, 55, 60, 65, 70, 75, 80, 85, 90, 95, 99 or 100% of the original activity, and useful ranges may be selected between any of these values (for example, from about 35 to about 100%, from about 50 to about 100%, from about 60 to about 100%, from about 70 to about 100%, from about 80 to about 100%, and from about 90 to about 100%). For example, preferred functional variants of the loline alkaloids described herein should retain pesticidal activity, that is, retain at least about 35, 40, 45, 50, 55, 60, 65, 70, 75, 80, 85, 90, 95, 99 or 100% of the pesticidal activity of the specified parent loline alkaloid. Similarly, preferred compositions of the invention are capable of supporting the maintenance of useful pesticidal activity of the pesticidal agent(s) they comprise, and can be said to retain pesticidal activity, ideally until applied using the methods contemplated herein.

Similarly, when used in respect of an insecticidal agent, such as an insecticidal composition, the phrase "retaining insecticidal efficacy" and grammatical equivalents and derivatives thereof is intended to mean that the agent still has useful insecticidal activity. Preferably, the retained activity is at least about 35, 40, 45, 50, 55, 60, 65, 70, 75, 80, 85, 90, 95, 99 or 100% of the original activity, and useful ranges may be selected between any of these values (for example, from about 35 to about 100%, from about 50 to about 100%, from about 60 to about 100%, from about 70 to about 100%, from about 80 to about 100%, and from about 90 to about 100%). For example, preferred functional variants of the present invention should retain insecticidal activity, that is, retain at least about 35, 40, 45, 50, 55, 60, 65, 70, 75, 80, 85, 90, 95, 99 or 100% of the insecticidal activity of the specified parent loline alkaloid or fraction comprising same. Similarly, preferred compositions of the invention are capable of supporting the maintenance of useful insecticidal activity of the insecticidal agent(s) they comprise, and can be said to retain insecticidal activity, ideally until applied using the methods contemplated herein.

The term "solvent" as used herein refers to one or more compounds used to dissolve or disperse another compound. The term "solvent system" as used herein refers to a mixture of one or more solvents, and in particular when used to refer to a solvent system present in a formulation contemplates the totality of solvents present in the formulation.

The general chemical terms used herein have their usual meanings.

The term "total hydroxyl groups" or "total OH groups" or grammatically equivalent variations as used herein refers to the number of moles of hydroxyl groups present in the subject composition, and thus includes the hydroxyl groups contributed by the solvent(s) and those contributed by any water or other components present.

The term "total nitrogen-containing groups" or grammatically equivalent variations as used herein refers to the number of moles of nitrogen-containing groups, such as ammonia, primary amine groups, secondary amine groups, and combinations thereof present in the subject composition, and thus includes the amine groups contributed by the solvent(s) or other components present.

The term "aliphatic" as used herein alone or in combination with other terms, unless indicated otherwise, refers to saturated and unsaturated, straight chain and branched, acyclic hydrocarbons. Those skilled in the art will appreciate that aliphatic groups include, for example, alkyl and alkenyl groups. In some embodiments, aliphatic groups have from 1 to 12, from 1 to 10, from 1 to 8, from 1 to 6, or from 1 to 4 carbon atoms.

The term "cycloaliphatic" as used herein alone or in combination with other terms, unless indicated otherwise, refers to saturated and unsaturated, nonaromatic, cyclic hydrocarbons. Those skilled in the art will appreciate that aliphatic groups include, for example, cycloalkyl groups. In some embodiments, cycloaliphatic groups have from 3 to 12, from 3 to 10, from 3 to 8, from 3 to 6, from 3 to 5 carbon atoms in the ring(s).

The term "alkyl" as used herein alone or in combination with other terms, unless indicated otherwise, refers to straight chain and branched chain saturated acyclic hydrocarbon groups. In some embodiments, alkyl groups have from 1 to 12, from 1 to 10, from 1 to 8, from 1 to 6, or from 1 to 4 carbon atoms. Examples of straight chain alkyl groups include, but are not limited to, methyl, ethyl, n-propyl, n-butyl, n-pentyl, n-hexyl, n-heptyl, and n-octyl. Examples of branched alkyl groups include, but are not limited to, isopropyl, iso-butyl, sec-butyl, tert-butyl, neopentyl, isopentyl, and 2,2-dimethylpropyl.

The term "alkenyl" as used herein alone or in combination with other terms, unless indicated otherwise, refers to straight and branched chain acyclic hydrocarbon groups having at least one double bond between two carbon atoms. In some embodiments, alkenyl groups have from 2 to 12, from 2 to 10, from 2 to 8, from 2 to 6, or from 2 to 4 carbon atoms. In some embodiments, alkenyl groups have one, two, or three carbon-carbon double bonds. Examples of alkenyl groups include, but are not limited to, vinyl, allyl, —CH═CH($CH_3$), —CH═C($CH_3$)$_2$, —C($CH_3$)═$CH_2$, and —C($CH_3$)═CH($CH_3$).

The term "cycloalkyl" as used herein alone or in combination with other terms, unless indicated otherwise, refers to saturated cyclic hydrocarbon groups. Cycloalkyl groups include mono-, bi- or tricyclic groups. In some embodiments, cycloalkyl groups have from 3 to 12, from 3 to 10, from 3 to 8, from 3 to 6, from 3 to 5 carbon atoms in the ring(s). In some embodiments, cycloalkyl groups have 5 or 6 ring carbon atoms. Examples of monocyclic cycloalkyl groups include, but are not limited to, cyclopropyl, cyclobutyl, cyclopentyl, cyclohexyl, cycloheptyl, and cyclooctyl. In some embodiments, the cycloalkyl group has from 3 to 8, from 3 to 7, from 3 to 6, from 4 to 6, from 3 to 5, or from 4 to 5 ring carbon atoms. Bi- and tricyclic ring systems include bridged, spiro, and fused cycloalkyl ring systems. Examples of bi- and tricyclic ring cycloalkyl systems include, but are not limited to, bicyclo[2.1.1]hexanyl, bicyclo[2.2.1]heptanyl, adamantyl, and decalinyl.

The term "acyl" as used herein alone or in combination with other terms, unless otherwise indicated, refers to a $R^{50}$C(O)— group, in which $R^{50}$ is selected from hydrogen, alkyl, cycloalkyl, and aryl. In some embodiments, $R^{50}$ is selected from alkyl, cycloalkyl, and aryl. In some embodiments, the acyl is $C_{1-20}$alkylC(O)—.

The term "aryl" as used herein alone or in combination with other terms, unless indicated otherwise, refers to cyclic aromatic hydrocarbon groups that do not contain any ring heteroatoms. Aryl groups include monocyclic, bicyclic and tricyclic ring systems. Examples of aryl groups include, but are not limited to, phenyl, azulenyl, heptalenyl, biphenyl, fluorenyl, phenanthrenyl, anthracenyl, indenyl, indanyl, pentalenyl, and naphthyl. In some embodiments, aryl groups have from 6-14, from 6 to 12, or from 6-10 carbon atoms in the ring(s). In some embodiments, the aryl groups are phenyl or naphthyl. Aryl groups include aromatic-aliphatic fused ring systems. Examples include, but are not limited to, indanyl and tetrahydronaphthyl.

The term "alkylene" as used herein alone or in combination with other terms, unless indicated otherwise, refers to a multivalent alkyl group. In some embodiments, the alkylene is a diradical of an alkyl group. In some embodiments, alkylene groups have from 1 to 6, from 1 to 4, from 2 to 6, from 2 to 4, from 1 to 3, or 2 or 3 carbon atoms. The radicals of an alkylene group may be on the same carbon atom or different carbon atoms of the group.

The term "arylaliphatic" as used herein alone or in combination with other terms, unless indicated otherwise, refers to an aliphatic group substituted with an aryl group. Examples of arylaliphatic groups include, but are not limited to, arylalkyl groups.

The term "arylalkyl" as used herein alone or in combination with other terms, unless indicated otherwise, refers to an alkyl group substituted with an aryl group. In some embodiments, the arylalkyl is an aryl$C_{1-6}$alkyl. Examples of arylalkyl groups include, but are not limited to, benzyl.

The term "alkoxy" as used herein alone or in combination with other terms, unless indicated otherwise, refers to an alkyl-O— group. In various embodiments, the alkoxy is a $C_{1-6}$alkyl-O— group.

The term "heterocyclyl" as used herein alone or in combination with other terms, unless indicated otherwise, is intended to include non-aromatic ring systems containing 3 or more ring atoms, of which one or more is a heteroatom. In some embodiments, the heteroatom is nitrogen, oxygen, or sulfur. In some embodiments, the heterocyclyl group contains one, two, three, or four heteroatoms. In some embodiments, heterocyclyl groups include mono-, bi- and tricyclic rings having from 3 to 16, from 3 to 14, from 3 to 12, from 3 to 10, from 3 to 8, or from 3 to 6 ring atoms. Heterocyclyl groups include partially unsaturated and saturated ring systems, for example, imidazolinyl and imidazolidinyl. Heterocyclyl groups include fused and bridged ring systems containing a heteroatom, for example, quinuclidyl. Heterocyclyl groups include, but are not limited to, aziridinyl, azetidinyl, azepanyl, diazepanyl, 1,3-dioxanyl, 1,3-dioxolanyl, isoxazolidinyl, morpholinyl, piperazinyl, piperidinyl, pyranyl, pyrazolidinyl, pyrrolinyl, pyrrolidinyl, tetrahydrofuranyl, tetrahydrothienyl, thiadiazolidinyl, and trithianyl.

The term "heteroatom" as used herein alone or in combination with other terms, is intended to include oxygen, nitrogen, sulfur, or phosphorus. In some embodiments, the heteroatom is selected from the group consisting of oxygen, nitrogen, and sulfur.

The term "halo" or "halogen" as used herein alone or in combination with other terms, unless indicated otherwise, is intended to include F, Cl, Br, and I.

The term "haloalkyl" as used herein alone or in combination with other terms, unless indicated otherwise, refers to an alkyl groups substituted with one or more halo.

The term "haloalkoxy" as used herein alone or in combination with other terms, unless indicated otherwise, refers to an alkyl-O— group wherein the alkyl is substituted with one or more halo.

In the context of the chemical groups referred to herein, prefixes of the formula $C_{n-m}$, wherein n and m are each an integer (for example, the prefixes $C_{1-12}$, $C_{1-6}$, $C_{2-6}$, $C_{1-5}$, $C_{1-4}$, $C_{2-4}$, $C_{1-3}$, $C_{2-4}$, etc.) in each case indicate the possible number of carbon atoms in the group. For example, $C_{1-6}$alkyl refers to an alkyl group having from 1 to 6 carbon atoms.

As used herein, the term "stable" when used in relation to a composition of the invention means a composition capable of supporting pesticidal efficacy for several weeks, preferably about one, about two, about three, about four, preferably about five, more preferably about six months, or longer. The term "stable" when used in relation to compositions of the invention comprising NFL also contemplates compositions formulated to reduce or prevent hydrolysis of NFL. For example, certain embodiments of stable compositions of the invention are formulated such that less than about 5%, 10%, 20%, 30%, 40%, 50%, 60%, 70%, 75%, 80%, 85%, 90%, 95%, 98%, 99% or about 100% of the NFL in the composition is degraded or hydrolysed after about 1, 2, 3, or 4 weeks or about 1, 2, 3, 4, 6, 9, 12, 18, 24, 36 or 48 months when stored at a temperature of about −20, 4, 10, 15, 20, 25, 30, 35, 40, 45, 50, 54, 55, or about 60° C., or at ambient temperature at 1 atm pressure. Useful ranges may be selected between any of these values. Preferably, the compositions of the invention are stable at ambient temperature (20° C.) at 1 atm pressure for a period of two years.

Methods and assays for testing the storage stability of compositions described herein are known in the art. Examples include the methods described in Pesticide Specifications, Manual on the development and use of FAO and WHO specifications for Pesticides, third revision of the first edition, World Health Organization and Food and Agriculture Organization of the United Nations, Rome 2010. A standard method of determining storage stability as described in the examples is to incubate the composition at a temperature of 54 OC (at 1 atm) for two weeks. The concentration of N-formylloline in the composition before and after storage is measured to determine the reduction in concentration of N-formylloline over the period of storage. Determining storage stability at elevated temperatures for relatively short periods may be a useful indicator of storage stability at lower temperatures for longer periods. For example, a reduction of less than about 10% N-formylloline when stored at 54° C. (at 1 atm) for two weeks may indicate that the composition is shelf stable at ambient temperature (about 20° C.) at 1 atm pressure over two years.

The term "surroundings" when used in reference to a plant subject to the methods and compositions of the present invention includes water, leaf litter, and/or growth media adjacent to or around the plant or the roots, tubers or the like thereof, adjacent plants, cuttings of said plant, supports, water to be administered to the plant, and coatings including seed coatings. It further includes storage, packaging or processing materials such as protective coatings, boxes and wrappers, and planting, maintenance or harvesting equipment.

The term "oral administration" includes oral, buccal, enteral and intra-gastric administration.

The term "parenteral administration" includes but is not limited to topical (including administration to any dermal, epidermal or mucosal surface), subcutaneous, intravenous, intraperitoneal, intramuscular and intratumoural (including any direct administration to a tumour) administration.

The term "(s)" following a noun contemplates the singular or plural form, or both.

The term "subject" is intended to refer to an animal, preferably a mammal, more preferably a mammalian companion animal or human. Preferred companion animals include cats, dogs and horses. Other mammalian subjects include an agricultural animal, including a horse, a pig, a sheep, a goat, a cow, a deer, or a fowl, or a laboratory animal, including a monkey, a rat, a mouse, a rabbit or a guinea pig. Other subjects include birds, such as ostriches, emus, hens, geese, turkeys, and ducks; and fresh- or salt-water fish.

The term "treat" and its derivatives should be interpreted in their broadest possible context. The term should not be taken to imply that a subject is treated until total recovery. Accordingly, "treat" broadly includes maintaining a subject's disease progression or symptoms at a substantially static level, increasing a subject's rate of recovery, amelioration and/or prevention of the onset of the symptoms or severity of a particular condition, or extending a patient's quality of life. The term "treat" also broadly includes the maintenance of good health for sensitive individuals and building stamina for disease, infection or infestation prevention.

The term "parasitic infection", as used herein, means an infection or infestation of external parasites (ectoparasites) or internal parasites (endoparasites) in or on a subject.

The term "nitrogen-containing groups" used herein, unless otherwise specified, means ammonia, a primary amine group, a secondary amine group, or combinations thereof.

2. Loline Alkaloids

Loline alkaloids are produced symbiotically during infection of grasses by endophytes, particularly Epichloë endophytes (which, following a nomenclature realignment now includes the previously separate anamorphic *Neotyphodium* genus). These endophytes are considered to be bioprotective, conferring pest, and possibly drought and disease protection to the symbionts of which they form part.

Loline alkaloids for use in the compositions of the invention may be purified from the endophyte by methods well known in the art, for example, by fractionation, filtration or sedimentation methodologies (e.g. centrifugation), whether in combination with one or more cell-lysis steps (for example, for intracellular loline alkaloids) or not (for example, for loline alkaloids that are secreted into growth media). Alternatively, loline alkaloids may be purified, isolated or extracted from plant material, such as seeds, foliage or stems of plants that have been infected with an endophyte using methods known in the art including those described above.

Loline alkaloids for use in the compositions of the invention may be synthesised or produced by fermentation using methods well known in the art.

In various embodiments, compositions comprising substantially purified loline alkaloids are specifically contemplated.

The inventors have established that loline alkaloids, in particular, N-formylloline (NFL), and particularly when at least partially purified, may be degraded over a prolonged period of storage. Without wishing to be bound by any theory, it is believed that NFL is degraded by hydrolysis to form loline.

3. Compositions of the Invention

In one aspect, the invention provides a composition comprising N-formylloline having the structure of Formula [II] as described above:

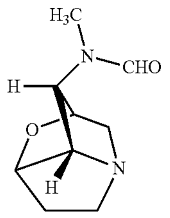

[II]

As used herein, "at least partially purified" when used in reference to a compound such as N-formylloline means that the N-formylloline has undergone at least one purification or isolation step aimed at removing one or more contaminants or undesired agents from the compound, such that the concentration of the compound in the at least partially purified state is greater relative to its concentration prior to at least partial purification. In one embodiment, at least partial purification contemplates an increase in relative concentration of the subject compound of at least 5% w/w in the partially purified state.

For example, at least partial purification contemplates the removal of one or more contaminants of a crude extract comprising one or more loline alkaloid compounds, particularly N-formylloline, such that the relative concentration of the one or more loline alkaloid compounds in the at least partially purified state is increased compared to its concentration prior to at least partial purification.

In another aspect, the invention provides a composition comprising N-formylloline having the structure of formula [II]

[II]

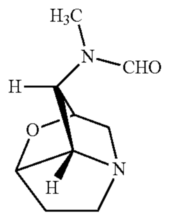

and one or more solvents, wherein the concentration of N-formylloline present in the composition is reduced by less than about 10% when stored at 54° C. (at 1 atm) for at least two weeks.

In various embodiments, the one or more loline alkaloids are at least partially purified loline alkaloids. For example, the one or more loline alkaloids are substantially pure, that is, substantially free from any other compounds. In one embodiment, the substantially pure loline alkaloids contain less than 10% impurities, for example, less than about 5% impurities, or less than about 1% impurities. Accordingly, the term "substantially pure" means that a sample of the relevant loline alkaloids contains more than 90% loline alkaloids, for example more than 95% loline alkaloids, or more than 99% loline alkaloids.

Without wishing to be bound by any theory, the present inventors have established that degradation of NFL increases with the presence of increasing molar ratio of hydroxyl groups, and/or increasing nucleophilicity coefficient of the system. The present inventors have established that the rate of degradation of NFL is reduced when NFL is formulated in a composition that has a molar ratio of total hydroxyl and nitrogen containing groups to NFL of less than about 20 and/or a nucleophilicity coefficient of less than about 0.6 eV, preferably 0.5 eV.

Compositions of the invention may comprise one or more solvents, for example, glycols or ethers thereof, amides, ketone comprising 3-8 carbon atoms, cycloaliphatic alcohols, or esters. For example, compositions of the invention may comprise one or more of dimethyllactamide (DMLA), dipropylene glycol methyl ether (e.g. DOWANOL™ DPM), ethylene glycol phenyl ether (e.g. DOWANOL™ EPH), acetophenone, cyclohexanol, or di-esters of adipic, glutaric and succinic acids. The present inventors have found that the rate of degradation of NFL is markedly reduced when NFL is formulated in a composition that is substantially free of solvents comprising hydroxyl groups, surfactants comprising hydroxyl groups and/or other compounds comprising hydroxyl groups.

The term "substantially free" as used herein with regard to compositions described herein being substantially free of solvents comprising hydroxyl and/or nitrogen containing groups, surfactants comprising hydroxyl and/or nitrogen containing groups, and/or other compounds comprising hydroxyl and/or nitrogen containing groups means that the composition comprises less than about 50%, 40%, 30%, 25%, 20%, 15%, 10%, 5%, 2% or less than about 1% by weight of solvents comprising hydroxyl and/or nitrogen containing groups, surfactants comprising hydroxyl and/or nitrogen containing groups, and/or other compounds comprising hydroxyl and/or nitrogen containing groups.

The term "substantially free" as used herein with regard to solvent(s) and/or surfactant(s) being substantially free of hydroxyl and/or nitrogen containing groups means that the solvent(s) and/or surfactant(s) compounds comprise less than about 1, 2, 3, 4 or about 5 hydroxyl and/or nitrogen containing groups per compound.

For example, a person skilled in the art can identify suitable solvents or combinations of solvents for use in the compositions of the invention by measuring the molar amount of hydroxyl and nitrogen-containing groups, determining the nucleophilicity coefficient, and/or testing the rate of degradation of NFL in the solvent or combination of solvents using the methods discussed above and other methodologies known in the art.

It is desirable that solvents and/or surfactants for use in the compositions of the invention are biodegradeable, agriculturally and/or horticulturally acceptable, non-toxic to humans and/or non-human animals and/or non-phytotoxic.

It is desirable for the compositions of the invention to have one or more of the following properties.

Preferably, compositions of the invention or diluted compositions of the invention have sufficient wetting ability when applied to a target locus, for example, plant foliage. For example, the composition penetrates and spreads rapidly across the foliage, no beading of the composition on the surface of the foliage occurs, and no residue remains on the surface of the foliage once the composition has dried.

Preferably, the one or more loline alkaloids penetrate the target locus following application of the composition. The uptake of loline alkaloids by plants treated with a composition of the invention may be determined using the methods discussed above.

In an alternative embodiment of the invention when a composition is formulated in a seed coating, seedlings grown from the coated seeds comprise a greater amount of the one or more loline alkaloids compared with seedlings grown from uncoated seeds.

Preferably, the one or more loline alkaloids remain substantially soluble in the compositions of the invention over a prolonged storage period. For example, the one or more loline alkaloids remain substantially soluble in the composition for a period of about 1, 2, 3, or 4 weeks or about 1, 2, 3, 4, 6, 9, 12, 18, 24, 36 or 48 months storage at a temperature of about −20, 4, 10, 15, 20, 25, 30, 35, 40, 45, 50, 54, 55, or about 60° C., or at ambient temperature.

Preferably, the compositions of the invention are substantially soluble in water or in other carriers or adjuvants used to dilute the composition prior to application.

4. Control of Pests

A composition of the invention, effective against pests, such as insects, and suitable for use in accordance with the invention, is identified as one which is effective at reducing the population of the target pest species by a statistically significant amount with respect to the control treatment against which the composition of the invention is compared. Such compositions can be considered as having pesticidal efficacy. As described herein, the reduction in the population of the target pest may be by various antagonistic mechanisms. For example, the composition may incapacitate, render infertile, inhibit the growth or development of, and/or preferably kill the pest, or may support or promote the growth and pesticidal efficacy of one or more other pesticidal agents also present, such as a pesticidal fungus present in a composition together with the loline alkaloids of the invention (whether separately, simultaneously, or sequentially). As such, the compositions of the invention may enable or support the ability of the pesticidal agent to incapacitate, render infertile, and/or preferably kill the pest. The compositions of the invention may also reduce the population of the target pest by rendering the environment, for example the plant to which the composition is applied or its surroundings, unfavourable for the pest. In this embodiment, the compositions may be considered to be acting as a repellent, and reducing the effective population of the target pest in the vicinity of the locus, such as a plant or its surroundings.

In various embodiments, compositions of the invention exhibit about 5, 10, 15, 20, 25, 30, 35, 40, 45 or more preferably at least about 50% pesticidal efficacy expressed as a percentage reduction of the population of the relevant insect species compared to the control treatment.

Pesticidal efficacy is desirable for a composition of the invention. Compositions of the invention may have additional characteristics to be suitable for use as a control agent. For example, the compositions of the invention should be able to be stored in effective form for a reasonable period, ultimately so as to allow it to be applied to the target locus, such as a plant or its surroundings, in a form and concentration that is effective as a control agent.

Those skilled in the art will recognise that the compositions of the invention may comprise or the methods of the invention may use one or more functional variants of one or more of the loline alkaloids. Combinations of loline alkaloids and functional variants thereof are also useful herein.

The inventors contemplate that the compositions disclosed herein will find particular utility as control compositions for topical and/or systemic application against a wide variety of agricultural, horticultural, medical or veterinary pests, insects and/or pathogens and in a wide variety of environments.

As will be apparent to those skilled in the art, the compositions of the invention may be formulated into suitable forms, such those described herein, for administration to a particular target locus.

Agricultural and Horticultural Uses

The present invention recognises that the agricultural and horticultural sectors of many countries, including for example that of the United States of America, of New Zealand, and many states of Europe, are faced with the problem of increasing pesticide resistance amongst plant pests. This is compounded under some regulatory regimes by a reduction in the availability of new chemical insecticides due to regulatory barriers, and the removal of existing chemical insecticides from the marketplace.

The use of pesticidal loline alkaloids made available by the present invention presents a solution to this problem.

The inventors contemplate that the compositions disclosed herein will find particular utility as control compositions for topical and/or systemic application in the horticultural and agriculture industries, such as by application to field crops, grasses, fruits and vegetables, lawns, trees, and/or ornamental plants. Other major crops include, but are not limited to, maize, wheat, soybean, cotton, rice, oilseed rape (canola), grapes, apples, pears, cherries, peaches, potatoes, tomatoes, brassicas, squash, tamarillos, strawberries, cucumbers, onions, capsicum, lettuce, sugar cane, sunflower, rye, cocoa, coffee, citrus fruits and pumpkin. The compositions disclosed herein may be formulated as a dust, powder or aerosol, or other aqueous or atomized form for killing a pest, or controlling a pest population. The compositions disclosed herein may be used prophylactically, or alternatively, may be administered to an environment once target pests have been identified in the particular environment to be treated. The compositions may comprise an individual loline alkaloid or may contain various combinations of the loline alkaloids disclosed herein.

Regardless of the method of application, the amount of the active component(s) is applied at a pesticidally-effective amount, which will vary depending on such factors as, for example, the specific target pests to be controlled, the specific environment or location, for example the plant, crop, or agricultural site to be treated, the environmental conditions, and the method, rate, concentration, stability, and quantity of application of the pesticidally-active composition. The formulations may also vary with respect to climatic conditions, environmental considerations, and/or frequency of application and/or severity of pest infestation.

The compositions described may be made by formulating compositions of the invention optionally together with one or more other agents, with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

Water-Dispersible Granules

In another embodiment, the compositions of the invention comprise a water dispersible granule. This granule comprises one or more compositions of the invention, optionally together with one or more other agents.

Powders, Dusts, and Dry Formulations

In another embodiment, the compositions of the invention comprise a wettable powder, dust, dry formulation, pellet, or colloidal concentrate. This powder comprises one or more compositions of the invention, optionally together with one or more other agents. Such dry forms of the compositions of the invention may be formulated to dissolve immediately upon wetting, or alternatively, dissolve in a controlled-release, sustained-release, or other time-dependent manner. Such compositions may be applied to, or ingested by, the target pest, and as such, may be used to control the numbers of pests, or the spread of such pests in a given environment.

Aqueous Suspensions

In another embodiment, the compositions of the invention comprise an aqueous suspension of one or more loline alkaloids, optionally together with one or more lysed or otherwise killed or non-viable endophyte cells, including one or more endophyte cells used to producing a loline alkaloid, including for example a culture filtrate, culture supernatant, culture media or extract or fraction therefrom. Such aqueous suspensions may be provided as a concentrated stock solution which is diluted prior to application, or alternatively, as a diluted solution ready-to-apply.

When the compositions of the invention comprise intact but dead cells, such compositions may be formulated in a variety of ways. They may be employed as wettable powders, granules or dusts, by mixing with various inert materials, such as inorganic minerals (phyllosilicates, carbonates, sulphates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Multifunctional Formulations

In certain embodiments, for example those when the control of multiple pest species is desired, the formulations described herein may also further comprise one or more other agents, such as one or more chemical pesticides, (such as chemical pesticides, nematocides, fungicides, virucides, microbicides, amoebicides, insecticides, etc.), and/or one or more loline alkaloids having the same, or different insecticidal activities or insecticidal specificities, as the insecticidal loline alkaloids identified herein. The compositions of the invention may also be used in conjunction with other treatments such as fertilizers, weed killers, cryoprotectants, surfactants, detergents, insecticidal soaps, dormant oils, polymers, and/or time-release or biodegradable carrier formulations that permit long-term dosing of a target area following a single application of the formulation. Likewise the formulations may be prepared into edible "baits" or fashioned into pests "traps" to permit feeding or ingestion by a target pest of the composition.

The compositions of the invention may also be used in consecutive or simultaneous application to an environmental site singly or in combination with one or more additional agents, including one or more insecticides, pesticides, chemicals, fertilizers, or other compounds.

The compositions of the invention may also include one or more carriers, including one or more agriculturally acceptable carriers. In one embodiment the carrier, such as an agriculturally acceptable carrier, can be solid or liquid. Carriers useful herein include any substance typically used to formulate agricultural composition.

In one embodiment the agriculturally acceptable carrier may be selected from the group comprising fillers, solvents, excipients, surfactants, suspending agents, spreaders/stickers (adhesives), antifoaming agents, dispersants, wetting agents, drift reducing agents, auxiliaries, adjuvants or a mixture thereof.

Compositions of the invention may be formulated as, for example, concentrates, solutions, aerosols, immersion baths, dips, emulsions, wettable powders, soluble powders, suspension concentrates, dusts, granules, water dispersible granules, microcapsules, pastes, gels and other formulation types by well-established procedures.

These procedures include mixing and/or milling of the active ingredients with agriculturally acceptable carrier substances, such as fillers, solvents, excipients, surfactants, suspending agents, spreaders/stickers (adhesives), antifoaming agents, dispersants, wetting agents, drift reducing agents, auxiliaries and adjuvants.

In one embodiment solid carriers include but are not limited to mineral earths such as silicic acids, silica gels, silicates, talc, kaolin, attapulgus clay, limestone, lime, chalk, bole, loess, clay, dolomite, diatomaceous earth, aluminas calcium sulphate, magnesium sulphate, magnesium oxide, ground plastics, fertilizers such as ammonium sulphate, ammonium phosphate, ammonium nitrate, and ureas, and vegetable products such as grain meals, bark meal, wood meal, and nutshell meal, cellulosic powders and the like. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

In one embodiment the carrier may also be liquid, for example, water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

In one embodiment surfactants include nonionic surfactants, anionic surfactants, cationic surfactants and/or amphoteric surfactants and promote the ability of aggregates to remain.

Spreaders/stickers promote the ability of the compositions of the invention to adhere to plant surfaces. Examples of surfactants, spreaders/stickers include but are not limited to Tween and Triton (Rhom and Hass Company), Deep Fried™, Fortune®, Pulse, C. Daxoil™, Codacide Oil®, D-C. Tate™, Supamet Oil, Bond®, Penetrant, Glowelt® and Freeway, Citowett™, Fortune Plus™, Fortune Plus Lite, Fruimec, Fruimec lite, alkali metal, alkaline earth metal and ammonium salts of aromatic sulphonic acids, e.g., ligninsulphonic acid, phenolsulphonic acid, naphthalenesulphonic acid and dibutylnaphthalenesulphonic acid, and of fatty acids, alkyl and alkylaryl sulphonates, and alkyl, lauryl ether and fatty alcohol sulphates, and salts of sulphated hexadecanols, heptadecanols, and octadecanols, salts of fatty alcohol glycol ethers, condensation products of sulphonated naphthalene and naphthalene derivatives with formaldehyde, condensation products of naphthalene or naphthalenesulphonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulphite waste liquors and methyl cellulose. Where selected for inclusion, one or more agricultural surfactants, such as Tween are desirably included in the composition according to known protocols.

Wetting agents reduce surface tension of water in the composition and thus increase the surface area over which a given amount of the composition may be applied. Examples of wetting agents include but are not limited to salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds.

As described above, the compositions of the present invention may be used alone or in combination with one or more other agricultural agents, including pesticides, insecticides, acaracides, fungicides or bactericides (provided such fungicides or bactericides are not detrimental or toxic to any fungi or bacteria present in the composition), herbicides, antibiotics, antimicrobials, nemacides, rodenticides, entomopathogens, pheromones, attractants, plant growth regulators, plant hormones, insect growth regulators, chemosterilants, microbial pest control agents, repellents, viruses, phagostimulents, plant nutrients, plant fertilisers and biological control agents. When used in combination with other agricultural agents the administration of the two agents may be separate, simultaneous or sequential. Specific examples of these agricultural agents are known to those skilled in the art, and many are readily commercially available.

Examples of plant nutrients include but are not limited to nitrogen, magnesium, calcium, boron, potassium, copper, iron, phosphorus, manganese, molybdenum, cobalt, boron, copper, silicon, selenium, nickel, aluminum, chromium and zinc.

Examples of antibiotics include but are not limited to oxytetracyline and streptomycin.

Examples of fungicides include but are not limited to the following classes of fungicides: carboxamides, benzimidazoles, triazoles, hydroxypyridines, dicarboxamides, phenylamides, thiadiazoles, carbamates, cyano-oximes, cinnamic acid derivatives, morpholines, imidazoles, beta-methoxy acrylates and pyridines/pyrimidines.

Further examples of fungicides include but are not limited to natural fungicides, organic fungicides, sulphur-based fungicides, copper/calcium fungicides and elicitors of plant host defences.

Examples of natural fungicides include but are not limited to whole milk, whey, fatty acids or esterified fatty acids.

Examples of organic fungicides include but are not limited to any fungicide which passes an organic certification standard such as biocontrol agents, natural products, elicitors (some of may also be classed as natural products), and sulphur and copper fungicides (limited to restricted use).

An example of a sulphur-based fungicide is Kumulus™ DF (BASF, Germany).

An example of a copper fungicide is Kocide™ 2000 DF (Griffin Corporation, USA).

Examples of elicitors include but are not limited to chitosan, Bion™, BABA (DL-3-amino-n-butanoic acid, β-aminobutyric acid) and Milsana™ (Western Farm Service, Inc., USA).

In some embodiments non-organic fungicides may be employed. Examples of non-organic fungicides include but are not limited to Bravo™ (for control of PM on cucurbits); Supershield™ (Yates, NZ) (for control of Botrytis and PM on roses); Topas™ 200EW (for control of PM on grapes and cucurbits); Flint™ (for control of PM on apples and cucurbits); Amistar™ WG (for control of rust and PM on cereals); and Captan™ Dithane™, Euparen™, Rovral™, Scala™, Shirlan™, Switch™ and Teldor™ (for control of Botrytis on grapes).

Examples of pesticides include but are not limited to azoxystrobin, bitertanol, carboxin, $Cu_2O$, cymoxanil, cyproconazole, cyprodinil, dichlofluamid, difenoconazole, diniconazole, epoxiconazole, fenpiclonil, fludioxonil, fluquiconazole, flusilazole, flutriafol, furalaxyl, guazatin, hexaconazole, hymexazol, imazalil, imibenconazole, ipconazole, kresoxim-methyl, mancozeb, metalaxyl, R-metalaxyl, metconazole, oxadixyl, pefurazoate, penconazole, pencycuron, prochloraz, propiconazole, pyroquilone, SSF-109, spiroxamin, tebuconazole, thiabendazole, toliflua-mid, triazoxide, triadimefon, triadimenol, triflumizole, triticonazole and uniconazole.

An example of a biological control agent other than a fungal strain described herein is the BotryZen™ biological control agent comprising Ulocladium oudemansii.

The compositions of the invention may also comprise a broad range of additives such as stabilisers and penetrants used to enhance the active ingredients. Additives may also include compositions which assist in maintaining stability in long term storage, for example unrefined corn oil and so called invert emulsions containing a mixture of oils and waxes on the outside and water, sodium alginate and actives on the inside.

As will be appreciated by those skilled in the art, it is important that any additives used are present in amounts that do not interfere with the effectiveness of the active agents.

The compositions may be prepared in a number of forms. One preparation comprises a powdered form of a composition of the invention which may be dusted on to a plant or its surroundings. In a further form, the composition is mixed with a diluent such as water to form a foam, gel or dip and applied appropriately using known protocols.

Compositions formulated for other methods of application such as injection, rubbing or brushing, may also be used, as indeed may any known art method. Indirect applications of the composition, for example to a plant surroundings or environment such as growth media, water, or as seed coatings are contemplated.

As discussed above, the concentration at which the compositions of the invention are to be applied may vary depending on the end use, physiological condition of the plant; type (including insect species), concentration and degree of pest infection; temperature, season, humidity, stage in the growing season and the age of plant; number and type of conventional insecticides or other treatments (including fungicides) being applied; and plant treatments (such as leaf plucking and pruning).

Similarly, it will be appreciated that the formulation of the compositions of the invention, for example, the concentration of the one or more loline alkaloids in the composition, the combination of different loline alkaloids in the composition, the solvents, surfactants, preservatives and/or antioxidants in the composition, the concentration of the solvents, surfactants, preservatives and/or antioxidants in the composition, and the addition of any diluents and/or adjuvants to a concentrate composition before application may vary depending on the factors mentioned above. In particular, the formulation of the compositions of the invention may vary depending on the species, physiological condition and growth stage of the plant or crops to which the composition is applied, and the species of target insect(s) or pest(s).

Other application techniques, including dusting, sprinkling, soaking, injection, seed coating, seedling coating, aerating, misting, atomizing, fumigating, aerosolizing, and the like, are also feasible and may be required under certain circumstances such as e.g., pests that cause root or stalk infestation, or for application to delicate vegetation or ornamental plants. These application procedures are also well-known to those of skill in the art.

The compositions of the present invention may also be formulated for preventative or prophylactic application to an area, and may in certain circumstances be applied to pets, livestock, animal bedding, or in and around farm equipment, barns, domiciles, or agricultural or industrial facilities, and the like.

The concentration of composition which is used for environmental, systemic, topical, or foliar application will vary widely depending upon the nature of the particular formulation, means of application, environmental conditions, and degree of activity.

The insecticidal formulation described above may be administered to a particular plant or target area in one or more applications as needed, with a typical field application rate per hectare ranging on the order of from about 100 to about 500 g/hectare of active ingredient, or alternatively, from about 500 to about 1000 g/hectare may be utilized. All application rates in the range of from about 100 g to about 1,000 g/hectare are contemplated to be useful in the management, control, and killing, of target insect pests using such insecticidal formulations. As such, rates of about 100, 125, 150, 200, 250, 300, 350, 400, 450, 500, 600, 700, 800, 900 g/hectare or about 1 kg/hectare or greater of active agent may be utilized in certain agricultural, industrial, and domestic applications of the pesticidal formulations described hereinabove.

Representative application rates for liquid compositions include application rates in the range of from about 50 mL to about 20 L active agent/hectare are contemplated. As such, rates of about 100, 200, 300, 400, 500, 600, 700, 800, 900 L/hectare, or about 1, 1.1, 1.2, 1.3, 1.4, 1.5, 1.6, 1.7, 1.8, 1.9, 2.0, 2.5, 3.0, 3.5 or about 4.5 L/hectare or greater of active agent may be utilized.

In a further aspect the present invention provides a method for controlling one or more pests, the method comprising applying to a plant or its surroundings a composition of the invention as described herein.

Young seedlings are typically most susceptible to damage from pests. Therefore, application of the compositions of the invention to freshly planted out crops, prior to emergence, is contemplated, as is application on emergence.

Repeated applications at the same or different times in a crop cycle are also contemplated. The compositions of the invention may be applied either earlier or later in the season. This may be over flowering or during fruiting. The compositions of the invention may also be applied immediately prior to harvest, or after harvest to rapidly colonise necrotic or senescing leaves, fruit, stems, machine harvested stalks and the like, for example to prevent pest colonisation. The compositions of the invention may also be applied to dormant plants in winter to slow pest growth on dormant tissues, and provide growth enhancement.

Application may be at a time before or after bud burst and before and after harvest. However, treatment preferably occurs between flowering and harvest. To increase efficacy, multiple applications (for example, 2 to 6 applications over the stages of flowering through fruiting) of the compositions of the invention is preferred.

Reapplication of the compositions of the invention should also be considered after rain. Using pest infectivity prediction models or infection analysis data, application of the BCA can also be timed to account for pest infection risk periods.

In various embodiments, the compositions of the invention comprising loline alkaloids are not deleterious to the plants or plant surroundings to which they are applied at dosage rates capable of achieving efficacy, such as pesticidal efficacy.

In certain aspects, compositions of the invention are used to control insect pests which are responsible for many pre- and post-harvest diseases which attack plant parts and reduce growth rate, flowering, fruiting, and production, and may cause death of afflicted plants. As used herein, insects pest include insects which directly feed on plants and insects which act as vectors for plant pathogens such as fungi and bacteria. It will be appreciated that by controlling insects hosts which act as vectors for plant pathogens, the incidence and/or severity of plant disease can be minimised.

Examples of the major insect pests afflicting horticultural crops include, but are not limited to, aphids, mealybugs, whiteflies, moths, butterflies, psillids, *thrips*, stink bugs, rootworms, weevils, leafhoppers and fruit flies, such as *Myzus persicae* (green peach aphid), *Aphis gossypii* Glover (melon/cotton aphid), *Rhopalosiphum maidis* (corn leaf aphid), *Aphis glycines* Matsumura (soybean aphid), *Brevicoryne brassicae* (cabbage aphid), *Anasa tristis* (squash bug); *Pseudococcus longispinus* (long tailed mealybug), *Pseudococcus calceolariae* (scarlet mealybug), *Pseudococcus viburni* (obscure mealybug), *Planococcus citri* (Citrus mealybug); *Trialeurodes vaporariorum* (greenhouse whitefly), *Bemisia tabaci* (silverleaf whitefly); *Plutella xylostella* (diamondback moth), *Citripestis sagittiferella* (citrus fruit moth), *Helicoverpa armigera* (tomato fruitworm or corn earworm), *Pectinophora gossypiella* (pink bollworm), *Phthorimaea operculella* (potato tuber moth), *Amyelois transitella* (Navel orangeworm), *Cydia pomonella* (codling moth), *Cnephasia jactatana* (black-lyre leafroller), *Epiphyas postvittana* (light-brown apple moth), *Grapholita molesta* (oriental fruit moth), *Ostrinia furnacalis* (Asian corn borer), *Ostrinia nubilalis* (European corn borer), *Scirpophaga excerptalis* (sugarcane top borer) *Diatraea saccharalis* (sugarcane borer), *Chilo plejadellus* (rice stalk borer), *Earias vitella* (spotted bollworm), *Earias insulana* (spiny bollworm), *Spodoptera frugiperda* (fall armyworm), *Spodoptera litura* (tobacco cutworm), *Melittia cucurbitae* (squash vine borer), *Teia anartoides* (painted apple moth), *Trichoplusia ni* (Cabbage looper); *Pieris rapae* (white butterfly); *Bactericera cockerelli* (tomato/potato psyllid), *Diaphorina citri* (Asian citrus psyllid), *Trioza erytreae* (African citrus psyllid); *Thrips obscuratus* (flower *thrips*), *Heliothrips haemorrhoidalis* (greenhouse *thrips*), *Thrips tabaci* (onion *thrips*), *Frankliniella williamsi* (Maize thrip); *Halyomorpha halys* (brown marmorated stink bug), *Oebalus pugnax* (rice stink bug), *Diabrotica virgifera virgifera* (western corn rootworm), *Diabrotica barberi* (northern corn rootworm), *Diabrotica undecimpunctata howardi* (southern corn rootworm), *Diabrotica virgifera zeae* (Mexican corn rootworm); *Pempheres affinis* (cotton stem weevil); *Nephotettix virescens* (green leafhopper), *Nilaparvata lugens* (brown planthopper); *Bactrocera tryoni* (Queensland fruit fly).

The methods of the invention have particular application to plants and plant products, either pre- or post-harvest. For example, the compositions may be applied to stored products of the type listed above including fruits, vegetables, cut flowers and seeds. Suitable application techniques encompass those identified above.

The compositions of the invention can potentially be used to treat or pretreat seeds or growth media, as opposed to direct application to a plant. The compositions of the invention also find use in plant processing materials such as protective coatings, boxes and wrappers.

Also encompassed by the present invention are plants, plant products, growth media and seeds treated directly with a composition of the invention.

Pharmaceutical and Veterinary Uses

The present invention provides methods of treating or preventing a pest, parasite or insect infection in a human or animal subject, comprising administering a therapeutically effective amount of a composition of the invention.

The pest, parasite or insect infection may comprise infection or infestation with any human or non-human animal endoparasites or ectoparasites.

External parasites or ectoparasites include, but are not limited to, bedbugs, fleas, flies, gnats, ticks, lice, and mites, such as, *Bovicola ovis* (Sheep louse); *Bovicola bovis; Haematopinus eurysternus* (short-nosed cattle louse); *Hypoderma* spp.; *Haematobia irritans exigua; Ctenocephalides* spp, such as *Ctenocephalides felis* (cat flea) and *Ctenocephalides canis* (dog flea), *Cochliomyia* spp.; *Chrysomya* spp.; *Linognathus vituli* (long nosed cattle louse); *Pediculus humanus capitis* (human head louse), *Pediculus humanus humanus* (human body louse), *Pthirus pubis* (crab louse), *Pulex irritans* (human flea), *Solenopotes capillatus* (tubercule-bearing louse); *Sarcoptes* spp. (mange mites), including *Sarcoptes scabiei cams, Sarcoptes scabiei suis, Sarcoptes scabiei bovis, Sarcoptes scabiei* var. *humani; Psoroptes* spp., including *Psoroptes ovis* and *Dermatophgoides* spp.; *Boophilus microplus*; and *Damaliniabovis.*

Internal parasites or endoparasites include, but are not limited to, protozoan parasites, such as *Plasmodium* spp.; *Trypanosoma* spp. and *Eimeria* spp., and parasitic worms (helminths). Helminths include, but are not limited to, cestodes (flatworms), nematodes (roundworms), and trematodes (flukes), such as, *Trichostrongyloidea*, including *Haemonchus contortus; Trichostrongylus* spp.; *Dictyocaulus* spp.; *Ascaridoidea*, including *Toxocara* spp.; *Strongylus* spp.; *Filarioidea*, including *Dirofilariaimmitis* and *Onchocerca* spp: *Trematoda*, including *Fasciolahepatica* and *Schistosoma* spp.; *Taenia* spp.; and *Moniezia* spp.; *Ostertagia* spp.; *Nematodirus* spp.; *Cooperia* spp.; *Bunostomum* spp.; *Oesophagostomum* spp.; *Chabertia* spp, *Trichuris* spp.; *Trichonema* spp.; *Capillaria* spp.; *Heterakis* spp.; *Toxocara* spp.; *Oxyuris* spp.; *Ancylostoma* spp.; *Uncinaria* spp.; *Toxascaris* spp.; and *Parascaris* spp.

The compositions of the invention may be administered alone or in admixture with one or more pharmaceutically or veterinarially acceptable excipients, carriers, or diluents selected with regard to the intended route of administration and standard pharmaceutical or veterinarian practice.

The term "pharmaceutically or veterinarially acceptable carrier" is intended to refer to a carrier including but not limited to an excipient, diluent or auxiliary that can be administered to a subject as a component of a composition of the invention. Preferred carriers do not reduce the activity of the composition and are not toxic when administered in doses sufficient to deliver an effective amount of a composition produced by the method of the invention thereof, or, when administered, of another pesticidal agent.

Compositions of the invention may be administered topically, orally or parenterally.

For example, the compositions may be administered orally, including sublingually, in the form of capsules, tablets, elixirs, solutions, suspensions, or boluses formulated to dissolve in, for example, the colon or duodenum. The formulations may comprise excipients, such as, starch or lactose or flavouring or colouring agents.

The compositions may be injected parenterally, for example, intravenously, intramuscularly or subcutaneously. For parenteral administration, the compositions may be formulated in a sterile aqueous solution or suspension that optionally comprises other substances, such as salt or glucose.

The compositions may be administered topically, in the form of sterile creams, gels, pour-on or spot-on formulations, suspensions, lotions, ointments, dusting powders, drug-incorporated dressings, shampoos, collars or skin patches. For example, the compositions of the invention may be incorporated into a cream comprising an aqueous or oily emulsion of polyethylene glycols or liquid paraffin; an ointment comprising a white wax soft paraffin base; a hydrogel with cellulose or polyacrylate derivatives or other suitable viscosity modifiers; a dry powder; aerosol with butane, propane, HFA, or CFC propellants; a dressing, such as, a tulle dressing, with white soft paraffin or polyethylene glycol impregnated gauze dressings or with hydrogel, hydrocolloid, or alginate film dressings. The compositions may also be administered intra-ocularly as an eye drop with appropriate buffers, viscosity modifiers (for example, cellulose derivatives), and preservatives (for example, benzalkonium chloride).

Pour-on or spot-on formulations may be prepared by dissolving the active ingredients in an acceptable liquid carrier vehicle, such as butyl digol, liquid paraffin or non-volatile ester with or without addition of a volatile component such as isopropanol. The formulations may comprise permeation enhancers including terpenes, solvents such as fatty acid esters, triglycerides, glycerol esters, or surfactants. The formulation can be in a form suitable for direct application or in the form of a concentrate that requires dilution with a suitable quantity of water or other diluent before application. Pour-on or spot-on formulations can be prepared by encapsulation to leave a residue of active agent on the surface of the animal.

For oral administration, capsules, boluses, or tablets may be prepared by mixing the compositions of the invention with a suitable finely divided diluent or carrier, additionally containing a disintegrating agent and/or binder such as starch, lactose, talc, or magnesium stearate. A drench formulation may be prepared by dispersing the active ingredients in an aqueous solution together with dispersing or wetting agents.

The compositions of the invention may be administered with animal feedstuffs or animal drinking water by, for example, dissolving, suspending, or dispersing the compositions or formulations in the feedstuffs or water.

For parenteral administration injectable formulations may be prepared in the form of a sterile solution or emulsion.

The compositions may be used in conjunction with other antiparasitic agents to widen the spectrum of activity or to prevent the buildup of resistance. Examples of other suitable anti-parasitic agents include macrocyclic lactones, including avermectines and milbemycins, such as, abamectin, cydectin, doramectin, eprinomectin, moxidectin, ivermectin, and milbemycin; benzimidazoles, such as, albendazole, cambendazole, fenbendazole, flubendazole, mebendazole, oxfendazole, parbendazole, and oxibendazole; pro-benzimidazoles, such as, febantel, thiophanate, and netobimin; salicylanilides, such as, closantel and niclosamide; imidazothiazoles, such as, butamisole. metronidazole, tinidazole, levamisole, pyrantel pamoate, or tetramisole; tetrahydropyrimidines, such as morantel; and hexahydropyrazinoisoquinolines, such as, praziquantel. The compositions may be administered with the other antiparasitic agents separately, simultaneously, or sequentially.

A person skilled in the art will be able to readily determine the appropriate dosage and frequency of administration for treating an animal with a parasitic infection.

The exact dosage will depend upon the frequency and mode of administration, the sex, age, weight and general condition of the animal treated, the nature and severity of the condition treated and any concomitant diseases to be treated and other factors evident to those skilled in the art.

The invention consists in the foregoing and also envisages constructions of which the following gives examples only and in no way limit the scope thereof.

EXAMPLES

Analytical Methods

Methods for identifying and determining of water content and the concentration of loline alkaloid in compositions described herein are well known in the art.

Other suitable methodologies will be apparent to a person skilled in the art on reading the specification. For example, other chromatographic methodologies such liquid chromatography, may be used. Other moisture analysis methodologies, for example loss on drying, may be used.

Coulometric Water Determination with Oven

Water content was measured via Karl Fischer (KF) coulometric titration with oven sampler.

The coulometric Karl Fischer method with oven is suitable for samples with low water content. Iodine is electrochemically generated, produced from iodide-containing reagents by anodic oxidation at a generator electrode directly in the titration vessel. The amount of consumed iodine and therefore the amount of water from the sample is proportional to the total current consumption (integral of the electric current over time).

The coulometric oven technique can be carried out with two different types of generator electrodes: with or without diaphragm. The diaphragm separates the smaller cathode compartment, where protons are reduced to hydrogen, from the larger anode compartment, where iodide is oxidised to iodine. Generator electrodes without diaphragm also have anode and cathode, but the compartments are not separated, in this case reagents that are specially designed for diaphragmless cells must be used. Coulometric Karl Fischer titrations in cells with diaphragm require two reagent solutions, an anolyte and a catholyte.

Many substances release their water only at high temperatures, making them inappropriate for direct KF titration. In this case water can be evaporated in a Karl Fischer oven operated at 100° C. to 250° C., depending on the sample. It is then transferred to the KF titration cell by purging with dry air or an inert gas. The coulometric titration cell is filled with the respective reagent solution. The carrier gas must be dried, for example with Molecular Sieve 0.3 nm.

Apparatus

Suitable equipment used in this method are: 801 Stirrer (Metrohm), 874 Oven Sampler Processor (Metrohm), 852 Titrando with diaphragmless titration cell (Metrohm), Software Tiamo (Metrohm), 6 ml vials with septum (Metrohm), and Analytical balance A T261 DeltaRange (Mettler).

Reagents

The following details are examples of suitable reagents, alternative equivalent reagents can be used. Coulometric cells without diaphragm combined with oven sampler require HYDRANAL Coulomat AG Oven and no catholyte solution is needed. For the SST of KF oven systems, 34693 HYDRANAL Water Standard KF Oven (140° C.-160° C.) and carry gas (dried air or inert gas) can be used.

Procedure

The recommended parameters using the Karl Fisher oven are shown in Table 1.

TABLE 1

| Recommended parameter using Karl Fisher oven Parameters | | |
|---|---|---|
| Flow of nitrogen/air | | 40 ml/min |
| Control parameter | relative stop drift | 5 μg/min |
| | end point | 50 mV |
| | stop criterion | relative drift |
| Titration parameter | extraction time | 5 min |
| Conditioning | start drift | 20 μg/min |
| Temperature of oven | | 120° C. |

The working conditions are optimised for each product analysed. The temperature chosen depends on the properties of the substance being investigated. The optimum oven temperature to remove the water is determined. The temperature must be high enough to drive off the water in the sample within 5 minutes. At the same time, the temperature must be low enough to prevent vaporisation of the sample matrix, which could interfere in the Karl Fischer titration, but high enough to prevent condensation in the transfer tubing.

Sublimating samples can block the transfer-line, therefor samples with tendency to sublimate should not be analysed by coulometer oven technique. When crystal water is present in the sample usually an increased temperature is needed.

Determination

After conditioning the titration cell, the blind consumption of the sample vessel is determined. The water content of the empty sample vessel is determined in triplicate. Same method conditions have to be applied for blind consumption as for sample(s).

For the determination of the water content usually a sample amount of approximately 100 mg is used. Usually a double determination is carried out.

Sequence and SST

The following injection sequence is proposed:

C $B_1$ $B_2$ $B_3$ $S_1$ $S_1$ $S_2$ $S_2$ SST

C=conditioning of titration cell

B=blind consumption (1, 2, 3)

S=sample(1, 2, . . . n)

SST=system suitability test

As SST (system suitability test) the HYDRANAL Water Standard KF Oven 140° C.-160° C. (or equivalent) is analysed. For SST, oven temperature is set at 140° C. and SST acceptance criteria: recovery of 95% to 105%.

Evaluation

The instrument measures the time and the electric current needed to reach the end point of the titration. The multiplication product (electric charge which is the integral of the electric current over time) is directly proportional to the amount of iodine generated and so to the water amount present in the sample.

Analysis of Loline by Gas Chromatography

NANL, NFL, NAL and Loline content was measured via gas chromatography-flame ionization detector (GC-FID).

Apparatus

Suitable equipment and conditions for analysis of loline by gas chromatography is shown in Table 2.

TABLE 2

| Suitable equipment and conditions | |
|---|---|
| Chromatograph: | Agilent 6890N |
| Chromatography Data System: | Agilent Chemstation |
| Detector: | FID, output voltage = 1 V |
| Column: | fused silica, 30 m length, 0.25 mm i.d. stationary phase: Rtx-5 Amine film thickness: 0.25 μm available from: Restek |
| Column temperature: | 60° C. (isothermal for 2 min) (80 to 220° C.) programmed with 8° C./min (220° C. to 300° C.) programmed with 30° C./min (300° C.) isothermal for 2 min |
| Detector temperature: | 300° C. |
| Injector temperature: | 300° C. |
| Spilt ratio: | 5:1 |
| Carrier gas: | helium, flow rate 2 ml/minute, (constant flow) |
| Make up gas | nitrogen, 30 ml/min |
| Size of sample | 1 μl of reference and test solution |
| Duration of chromatography: | approx. 27 minutes |
| Internal standard: | Dibutyl succinate |
| Solvent: | Acetonitrile |

Preparation of Reference and Test Solutions

The reference substances are a technical mixture of loline, or reference material of each loline. The internal standard (IS) used is dibutyl succinate and the solvent is 2% v/v $NH_3$ (conc. in water) in Acetonitrile. The reference solutions contains approximately 70 μg/ml Lolines (Sum of NANL, NFL, NAL and Loline) and 300 μg/ml IS.

Analysis of Nucleophilicity

The local nucleophilic characteristics within simple chemical systems can be simulated based on the well-established nucleophilicity index methodology [*Journal of Molecular Structure: THEOCHEM,* 2009, 895, 86-91; *Computational and Theoretical Chemistry,* 2012, 980, 49-55]. The resulting coefficients constitute an extension of the global nucleophilicity descriptor, N introduced for reagents in cycloaddition reactions and other organic molecules [*Journal of Organic Chemistry* 2008, 73, 4615-4624; *Journal of Molecular Structure* (*THEOCHEM*), 2008, 865, 68-72].

The local nucleophilic coefficients in Table 3, reflect the nucleophilic strength of the corresponding circled atom. They are calculated based on the Fukui function (calculated at the DFT/B3LYP/6-31G (d, p) level of theory using the nucleophilicity index N), which is a function describing the electron density in the frontier molecular orbitals of a molecule upon applying specific electronic changes. The values tabulated correspond to the nucleophilicity coefficients for the most relevant atoms in the respective solvent candidates. The higher the value, the more nucleophilic. The trend observed correlates with that observed for NFL stability, particularly when taken together with the OH count analysis (i.e. glycerol, entry 3 has a significantly higher coefficient that that for DMLA, entry 5). These calculations are performed on the single molecule (simulated in the gas phase) and could be influenced by further solvent interactions.

TABLE 3

Nucleophilicity coefficients for most relevant atoms in solvents.

| Entry | Solvent Name | Solvent Structure | Nucleophilicity Coefficient (eV) |
|---|---|---|---|
| 1 | Ethylene Glycol | 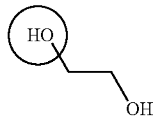 | 0.50 |
| 2 | Propylene Glycol | 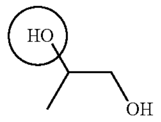 | 0.53 |
| 3 | Glycerol | 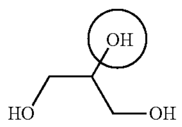 | 0.52 |
| 4 | Benzylalcohol | 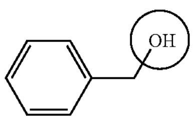 | 0.20 |
| 5 | DMLA | 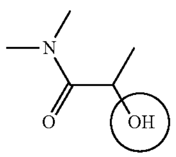 | 0.28 |

TABLE 3-continued

Nucleophilicity coefficients for most relevant atoms in solvents.

| Entry | Solvent Name | Solvent Structure | Nucleophilicity Coefficient (eV) |
|---|---|---|---|
| 6 | PEG | 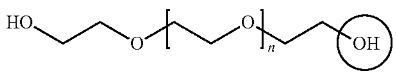 | 0.29 |
| 7 | MPEG | 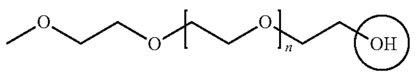 | 0.25 |

Specific Methodology

The geometries of all molecules were optimized (analysed) at the DFT-B3LYP/6-31G(d,p) [*Journal of Chemical Physics,* 1993, 98, 5648-5652; *Physical Review B,* 1988, 37, 785-789] level of theory using the Gaussian09 program [*Gaussian Inc.,* 2013, Wallingford, CT]. Energy calculations using unrestricted open shell method for the N−1 electronic species were done at the same level of theory on the N-electron optimized geometries obtained previously. The condensed Fukui functions were calculated using Natural population analysis (NPA) [*Chemical Review,* 1988, 88, 899-926] as implemented in Gaussian09 program.

The Gaussian analysis generated HOMO and LUMO energies: HOMO (Highest Occupied Molecular Orbital) and LUMO (Lowest Occupied Molecular Orbital) are mathematical functions that describe the behavior of electrons in the most relevant reactive states of a molecule. HOMO and LUMO energies were used to calculate the nucleophilicity coefficient (measured in electron volts, eV) using methods known in the art.

The nucleophilicity of a solvent system containing more than one solvent can be calculated using the same method.

Example 1—Loline Stability Analysis

This example demonstrates the chemical stability of loline alkaloids in different solvent systems.

Loline botanical extracts can be purified according to the method described in published international patent application WO 2016/091987, the entirety of which is incorporated herein by reference. Purified loline botanical extract (A1) and technical grade lolines (crude botanical extract), (TGAI), (A2), were tested in different solvent systems, and submitted to elevated temperature storage for chemical stability testing. Tables 4 and 5 shows the loline content in A1 and A2 samples respectively.

Both samples contain a mixture of three loline alkaloids, N-acetyl norloline (NANL), N-acetyl loline (NAL), and N-formyl loline (NFL), which are plant-derived natural compounds. Analytics were performed using GC-FID to determine the amount of NANL, NAL, NFL and loline. A2 also contains other natural components like carbohydrates which were not analysed here.

TABLE 4

Loline content in A1.

| | N-Acetyl Norloline NANL [% w/w] | N-Formyl Loline NFL [% w/w] | N-Acetyl Loline NAL [% w/w] | Loline [% w/w] | Sum of Lolines [% w/w] |
|---|---|---|---|---|---|
| A1 | 8.50 | 65.69 | 15.10 | 2.95 | 92.2 |
| % of total lolines before start of storage test | 9.2 | 71.2 | 16.4 | 3.2 | 100 |

TABLE 5

Loline content in A2.

| | N-Acetyl Norloline NANL [% w/w] | N-Formyl Loline NFL [% w/w] | N-Acetyl Loline NAL [% w/w] | Loline [% w/w] | Sum of Lolines [% w/w] |
|---|---|---|---|---|---|
| A2 | 8.13 | 15.81 | 4.92 | 0.94 | 29.8 |
| % of total lolines before start of storage test | 27.3 | 53.1 | 16.5 | 3.2 | 100 |

Loline solutions, 20% (w/w) concentrated, were prepared in various different solvents (solo systems, no solvent mixtures were evaluated). Only the systems in which the lolines dissolved (by visual inspection) at the concentration of 20% (w/w) were submitted to elevated temperature storage testing.

Figure 3:
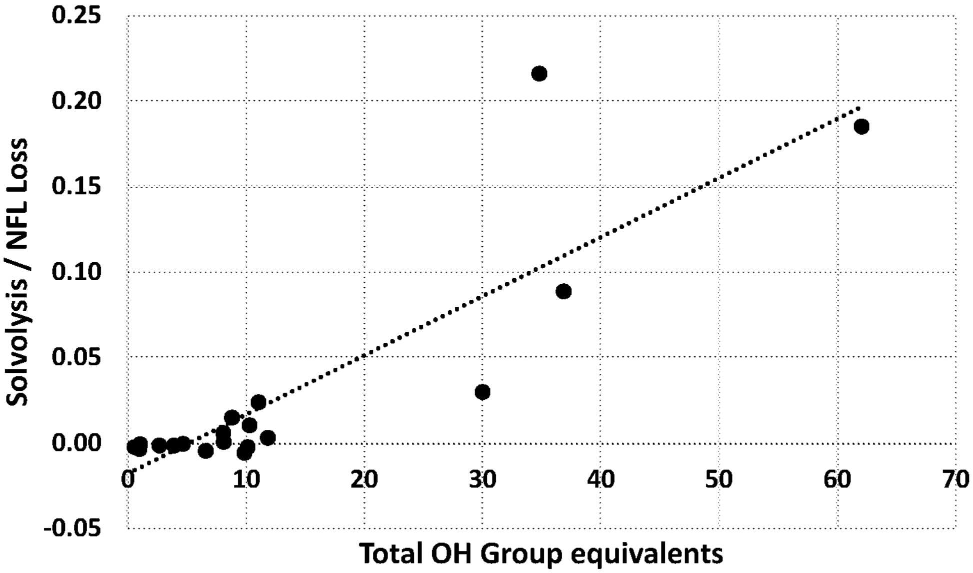
FIG. 3 shows the solvolysis relative to total hydroxyl group equivalents from water and solvents (20% w/w loline solutions prepared with purified extract).
Figure 4:
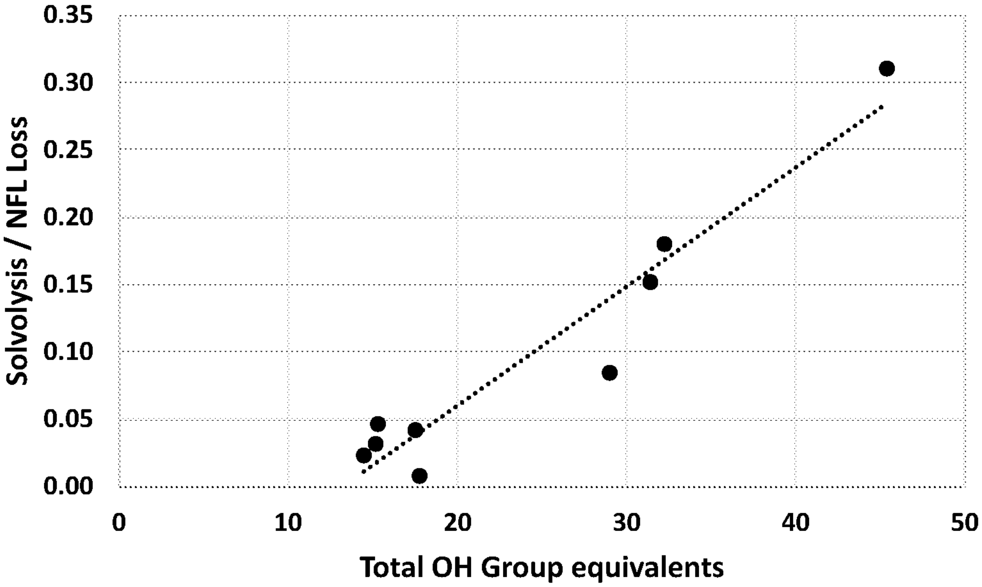
FIG. 4 shows a graph depicting the solvolysis vs total hydroxyl group equivalents for 20% w/w loline solutions prepared with crude extract as described herein in the Examples.

The degradation of NFL in A1 and A2 after storage of 2 weeks at 54° C. was measured. The results are shown in tables 6 and 7 respectively. FIGS. 3 and 4 show the degradation of NFL relative to total hydroxyl group equivalents from solvents and water for purified and crude extracts respectively. Equivalent OH groups in solvent to NFL is calculated by dividing the number of moles of OH groups in the solvent(s) by the number of moles of NFL. Equivalent water to NFL is calculated by dividing the number of moles of water by the number of moles of NFL. Total equivalent OH groups to NFL is the sum of equivalent OH groups in solvent to NFL and equivalent water to NFL.

TABLE 6

Chemical stability (NFL loss) after 2 weeks @ 54° C. of 20% (w/w) loline solutions prepared from purified extract (A1).

| Solvent | Moles OH groups in solvent in composition | Equivalent OH groups in solvent to NFL | Measured total water content wt % | Moles water | Equivalent water to NFL | Total equivalent OH groups to NFL | Degradation after 2 weeks (54° C.) % |
|---|---|---|---|---|---|---|---|
| DMSO | 0.000 | 0.000 | 1.290 | 0.717 | 0.994 | 0.994 | −0.34 |
| Acetonitrile | 0.000 | 0.000 | 1.310 | 0.728 | 1.009 | 1.009 | −0.07 |
| Acetophenone | 0.000 | 0.000 | 1.370 | 0.761 | 1.056 | 1.056 | −0.06 |
| Cyclohexanol | 7.988 | 11.078 | 0.990 | 0.550 | 0.763 | 11.841 | 0.32 |
| Benzyl alcohol | 7.398 | 10.259 | 1.040 | 0.578 | 0.801 | 11.061 | 2.40 |
| Glycerol 100% | 26.061 | 36.142 | 0.940 | 0.522 | 0.724 | 36.867 | 8.86 |
| Dowanol DPM | 5.398 | 7.486 | 0.820 | 0.456 | 0.632 | 8.118 | 0.06 |
| Propylene glycol | 21.053 | 29.196 | 1.040 | 0.578 | 0.801 | 29.997 | 2.99 |
| PEG300 | 5.333 | 7.396 | 0.900 | 0.500 | 0.693 | 8.090 | 0.60 |
| PEG400 | 4.000 | 5.547 | 1.340 | 0.744 | 1.032 | 6.580 | −0.45 |
| MPEG350 | 2.286 | 3.170 | 0.960 | 0.533 | 0.740 | 3.910 | −0.14 |
| MPEG550 | 1.455 | 2.017 | 0.860 | 0.478 | 0.663 | 2.680 | −0.14 |
| Dowanol EPH | 5.789 | 8.028 | 1.000 | 0.556 | 0.770 | 8.798 | 1.50 |
| DMLA | 6.829 | 9.471 | 0.880 | 0.489 | 0.678 | 10.149 | −0.23 |
| Purasolv EL | 6.772 | 9.392 | 1.170 | 0.650 | 0.901 | 10.293 | 1.04 |
| Triethylcitrate | 2.896 | 4.016 | 0.850 | 0.472 | 0.655 | 4.671 | −0.05 |
| Butylbenzoate | 0.000 | 0.000 | 0.750 | 0.417 | 0.578 | 0.578 | −0.24 |
| Glycerine carbonate | 6.780 | 9.402 | 0.600 | 0.333 | 0.462 | 9.864 | −0.56 |
| DL-Lactic acid | 17.762 | 24.633 | 13.200 | 7.333 | 10.170 | 34.803 | 21.61 |
| Water | 44.444 | 61.636 | 0.546 | 0.303 | 0.421 | 62.057 | 18.51 |

TABLE 7

Chemical stability (NFL loss) after 2 weeks @ 54° C. of 20% (w/w) loline solutions prepared with crude extract (A2), which contains about 20% water.

| Solvent | Moles OH groups in solvent | Equivalent OH groups in solvent to NFL | Measured total water content wt % | Moles water | Equivalent water to NFL | Total equivalent OH groups to NFL | Degradation after 2 weeks (54° C.) % | Nucleo-philicity (eV) |
|---|---|---|---|---|---|---|---|---|
| Glycerol 100% | 11.076 | 19.340 | 13.300 | 7.389 | 12.902 | 32.242 | 18.03 | 0.52 |
| Propylene glycol | 8.947 | 15.623 | 13.800 | 7.667 | 13.387 | 29.010 | 8.49 | 0.53 |
| PEG300 | 2.267 | 3.958 | 11.700 | 6.500 | 11.350 | 15.308 | 4.67 | 0.29 |
| PEG400 | 1.700 | 2.968 | 15.000 | 8.333 | 14.551 | 17.519 | 4.23 | 0.29 |
| MPEG350 | 0.971 | 1.696 | 13.900 | 7.722 | 13.484 | 15.180 | 3.21 | 0.25 |
| MPEG550 | 0.618 | 1.079 | 13.800 | 7.667 | 13.387 | 14.466 | 2.35 | 0.25 |
| DMLA | 2.903 | 5.068 | 13.100 | 7.278 | 12.708 | 17.776 | 0.83 | 0.28 |
| Glycerine carbonate | 2.881 | 5.031 | 13.200 | 7.333 | 12.805 | 17.836 | 21.19 | — |
| DL-Lactic acid | 7.549 | 13.181 | 18.800 | 10.444 | 18.237 | 31.418 | 15.22 | — |
| Water | 18.889 | 32.982 | 12.800 | 7.111 | 12.417 | 45.399 | 31.06 | — |

Not all of the good solvents identified for A1 (Purified loline botanical extract) were able to dissolve A2 (crude extract/TGAI) as well at tested concentration. Water content of all systems was measured via Karl Fisher titration.

From the data for A1, it is seen that the higher the total hydroxyl equivalence to NFL, and the more nucleophilic, the higher is NFL degradation. All 20% loline non-aqueous concentrated solutions prepared from A1 showed similar amounts of water traces (around 1%).

All 20% loline concentrated solutions prepared from crude extract (A2) showed a water content varying between 11.7% and 18.8%. A similar trend was observed as with A1 the higher the total OH equivalence to NFL and the more nucleophilic, the higher was NFL degradation.

The level of NFL degradation to loline depends on the molar equivalence of total OH groups to NFL, and the nucleophilicity coefficient of the system (the higher OH equivalence and more nucleophilic the system is, the higher the degradation under same testing conditions). Very little NFL degradation was observed in DMLA. Some solvents like DMLA or MPEGS show some kind of stabilizing effect with TGAI.

NANL and NAL components were chemically stable under tested conditions.

When present in the technical grade (crude extract) A2, NFL undergoes more decomposition in comparison to that present in the purified sample A1 under same testing conditions. Without wishing to be bound by any theory, the inventors believe other components in the crude extract (i.e. carbohydrates etc.) may affect stability.

Example 2—Effect of Water Scavenger

This example investigates stability of NFL in dimethyllactamide (DMLA).

Example 4—Lolines in Water

This example investigates degradation of NFL into Loline in the presence of water, and the roles of pH and temperature on the degradation kinetics.

1% w/w solutions of purified loline extract at various pH and 0.2M buffers were used in this investigation. The buffers used at various pH are shown in Table 9. The solutions were maintained at 54° C. (±1° C.) and 70° C. (±1° C.) and pH remained at the target pH (±0.2 pH units). Samples were taken periodically over a 2-3 week period and analysed by GC-FID to determine NFL strength.

TABLE 9

Buffer recipes prepared for NFL hydrolytic stability study.

| | pH | | | | |
|---|---|---|---|---|---|
| | 2.6 | 4 | 4 | 6 | 10 |
| Components | Citric Acid monohydrate/ Sodium/ phosphate dibasic | Citric Acid monohydrate/ Trisodium citrate dihydrate | Sodium acetate trihydrate/ Acetic Acid | Sodium phosphate dibasic dehydrate/ Sodium phosphate monobasic monohydrate | Sodium bicarbonate/ Sodium carbonate decahydrate |
| Concentration | 0.2M | 0.2M | 0.2M | 0.2M | 0.2M |

A 1% w/w solution at 70° C. in DMLA was used. Before increasing the temperature to 70° C. the solution was treated with 3 Å molecular sieves (water scavengers) to ensure the system was water free. Table 8 shows A1 stability in DMLA (1% w/w) after 13 days at 70° C.

TABLE 8

A1 stability in DMLA (1% w/w) after 13 days at 70° C.

| | N-Acetyl Norloline NANL [% w/w] | N-Formyl Loline NFL [% w/w] | N-Acetyl Loline NAL [% w/w] | Loline [% w/w] | Sum of Lolines [% w/w] |
|---|---|---|---|---|---|
| A1 in DMLA, 1% - Day 1 | 0.07 | 0.63 | 0.14 | 0.02 | 0.9 |
| Percentage total lolines | 8.1 | 73.3 | 16.3 | 2.3 | 100 |
| A1 in DMLA, 1% - Day 13 | 0.07 | 0.63 | 0.14 | 0.02 | 0.9 |
| Percentage total lolines | 8.1 | 73.3 | 16.3 | 2.3 | 100 |

No degradation was observed in A1 after 13 days of testing at 70° C. when residual water was removed with molecular sieves.

Example 3—Lolines in Solid Formulations

This example investigates A2 stability in solid formulation.

A2 was dried on a Halogen Moisture Analyzer HR73 from Mettler Toledo at 80° C. Once the weight had stabilized, corresponding to about 19.4% (w/w) weight loss, it was assumed that all water was removed. The sample was collected and put under storage testing for 2 weeks at 54/−18° C.

No NFL degradation was observed indicating chemically stability.

Figure 2:
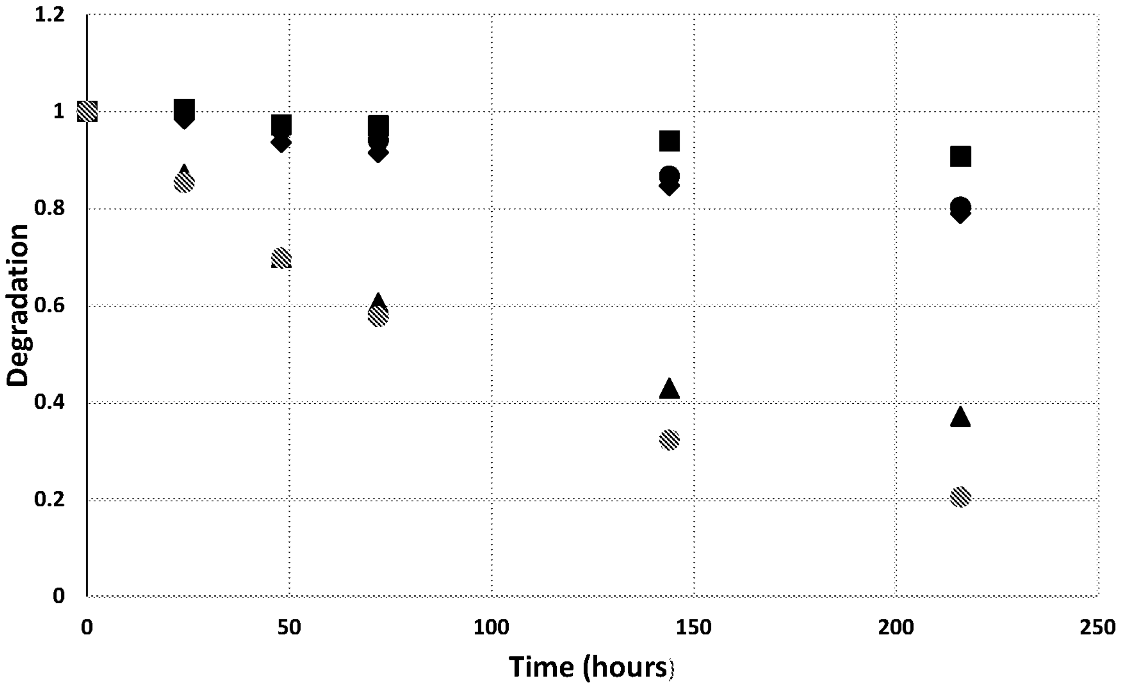

The degradation of NFL to loline at 70° C. and 50° C. is shown in FIGS. 1 and 2, respectively. Only data on NFL were reported as NANL and NAL components were chemically stable during the investigations except for pH 2 and 10 where small degradation was observed starting at 24 h.

At 70° C., the combination of pH 4 and acetic acid derived buffer resulted in the greatest stability with lowest degradation of NFL to loline over a period of 170 hours. Increasing or decreasing pH leads to significant decrease in stability. The citric acid buffer at pH 4 resulted in lower stability. At pH 2.6, the stability of NFL plateaus after approximately 100 hours.

At 50° C., the overall degradation rates were reduced and the general trends as a function of pH remained consistent.

At both 50° C. and 70° C., the buffer used in the system affects the conversion of NFL to loline. The citric acid based system showed higher degradation than the acetic acid derived buffer.

Example 5—Loline Efficacy Analysis

This example investigates the efficacy of formulations comprising NFL in different solvent systems following storage.

Formulations comprising 20% lolines in various solvent systems are prepared and subjected to accelerated storage at 54° C. for two weeks as described in Example 1. The solvents that tested are listed in Table 11.

After storage, formulations are diluted in water to a concentration of 250 ppm total loline alkaloids and promptly tested for efficacy in contact bioassays with green peach aphids. Formulations comprising the equivalent amount of solvent diluted in water are prepared as controls.

A composition comprising fresh A2 not subjected to accelerated storage conditions and diluted to 250 ppm is included as a positive control. Three plates comprising 30 aphids per plate are treated with each diluted formulation.

TABLE 11

| Solvents tested | |
|---|---|
| Solvent no. | Solvent |
| 1 | Water |
| 2 | Glycerol |
| 3 | DL-Lactic acid |
| 4 | DMSO |
| 5 | acetonitrile |
| 6 | Butyl benzoate |
| 7 | Acetophenone |
| 8 | Cyclohexanol |
| 9 | Benzyl alcohol |
| 10 | Dowanol DPM |
| 11 | Propylene glycol |
| 12 | PEG300 |
| 13 | PEG400 |
| 14 | MPEG350 |
| 15 | MPEG550 |
| 16 | Dowanol EPH |
| 17 | DMLA |
| 18 | Purasolv EL |
| 18 | Triethylcitrate |
| 20 | Butyl benzoate |
| 21 | Glycerine carbonate |

Bok choy leaves are cut and immersed in water with dilute hydrogen peroxide for 1 hour. Leaves are then dried and placed on cooled, small agar plates, upside down. Aphids from a colony maintained on wheat plants are placed upon small agar plates with the bok choy cuttings and then sprayed using a Potter spray tower. Aphids are sprayed with the treatments using a calibrated and level Potter tower to give an equal distribution of samples over the plate. The spray tower is washed with two runs of ethanol and a run of water between each treatment. After spraying, plates are topped with meshed lids and sealed with parafilm. Plates are then incubated for 72 hours at 23° C. with 84% humidity, 16 h light/8 h dark. Aphids are scored for morbidity and mortality every 24 h.

The results show that aphid mortality is less with formulations comprising solvents 1-3.

INDUSTRIAL APPLICATION

The compositions and methods of the invention have utility in a wide range of agricultural, horticultural, medical and veterinary applications, such as providing horticulturalists with a useful means of controlling plant pests, and providing therapies for the treatment or prevention of insect infection or infestation in humans or non-human animals.

The invention claimed is:

1. A composition comprising at least about 10 g/L of one or more loline alkaloids having the structure of Formula [I]:

[I]

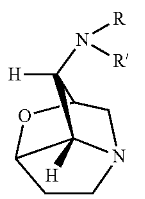

wherein R═H or $CH_3$ and R'═H, $CH_3$, CHO or $COCH_3$, the one or more loline alkaloids comprising N-formylloline having the structure of Formula [II]:

[II]

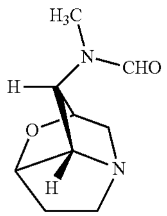

and one or more solvents; wherein a) the molar ratio of total hydroxyl groups and nitrogen-containing groups to N-formylloline of the composition is less than about 20, or b) the molar ratio of total hydroxyl groups and nitrogen-containing groups to N-formylloline of the composition is greater than about 20, and wherein the nucleophilicity coefficients of the hydroxyl groups or nitrogen-containing groups of the composition are less than about 0.6 eV;

wherein the nitrogen-containing groups are selected from ammonia, a primary amine group, a secondary amine group, or mixtures thereof;

wherein the one or more solvents are selected from the group consisting of:

1) polyalkylene glycols, or ethers or esters thereof;
2) propylene glycol;
3) dimethyllactamide;
4) cyclohexanol;
5) benzyl alcohol;
6) glycerine carbonate;
7) butyl benzoate and/or ethyl lactate; and
8) triethylcitrate, wherein at least about 50% w/w of the total solvents of the composition consists of the one or more solvents.

2. The composition of claim 1 wherein the N-formylloline having the structure of Formula [II] is at least partially purified or isolated.

3. The composition of claim 1 wherein the concentration of N-formylloline present in the composition is reduced by less than about 10% when stored at 54° C. at 1 atm for at least two weeks.

4. The composition of claim 1, wherein the nucleophilicity coefficients of the hydroxyl or nitrogen-containing groups of the one or more solvents are less than 0.5 eV.

5. The composition of claim 1, wherein the composition further comprises one or more loline alkaloids selected from the group consisting of loline, norloline, N-acetylloline (NAL), N-acetylnorloline (NANL), and N-methylloline (NML), N-formylnorloline, or a combination of any two or more thereof.

6. The composition of claim 1, wherein the composition comprises N-formylloline (NFL), N-acetylloline (NAL), and N-acetylnorloline (NANL).

7. The composition of claim 1, wherein the weight ratio of [NANL]:[NFL]:[NAL] is from about 1:12:1 to about 2:5:3.

8. The composition of claim 1, wherein the composition comprises at least about 5 g/L of N-formylloline having the structure of Formula [II].

9. The composition of claim 1, wherein the composition comprises at least about 50 g/L of loline alkaloids having the structure of Formula [I].

10. The composition of claim 1, wherein the N-formylloline having the structure of Formula [II] and/or the one or more loline alkaloids having the structure of Formula [I] are pure.

11. The composition of claim 1, wherein the composition is free of non-loline plant derived alkaloids or material.

12. The composition of claim 1, consisting essentially of N-formylloline, optionally together with one or more loline alkaloids of Formula [I], and one or more solvents.

13. The composition of claim 1, wherein the molar ratio of total hydroxyl groups and nitrogen-containing groups to N-formylloline of the composition is less than about 10; wherein the nitrogen-containing groups are selected from ammonia, a primary amine group, a secondary amine group, or mixtures thereof.

14. The composition of claim 1, wherein the one or more solvents comprises at least about 10% w/w of the composition.

15. The composition of claim 1, wherein the one or more solvents are polyalkylene glycols, or ethers or esters thereof, of the formula $R^{10}O—[(C_{1-6}alkylene)O]_x—R^1$, wherein $R^1$ and $R^{10}$ are each independently selected from hydrogen, aliphatic, cycloaliphatic, acyl, aryl, or arylaliphatic, and x is an integer from 2 to 140.

16. The composition of claim 1, wherein the one or more solvents are selected from the group consisting of dimethyllactamide, dipropylene glycol methyl ether, cyclohexanol, polyethylene glycol, polyethylene glycol methyl ether, butyl benzoate, triethylcitrate, glycerine carbonate, ethylene glycol, propylene glycol, and benzyl alcohol.

17. The composition of claim 1, wherein the one or more solvents are selected from the group consisting of dimethyllactamide, polyethylene glycol having a molecular weight of from 100 to 6000, a polyethylene glycol methyl ether having a molecular weight of from 100 to 1000, butyl benzoate, triethylcitrate, glycerine carbonate, and benzyl alcohol.

18. The composition of claim 1, wherein one of the one or more solvents is dimethyllactamide.

19. The composition of claim 1, wherein the nucleophilicity coefficients of the hydroxyl groups or nitrogen-containing groups of the one or more solvents are less than 0.3 eV; wherein the nitrogen-containing groups are selected from ammonia, a primary amine group, a secondary amine group, or mixtures thereof.

20. The composition of claim 1, wherein the one or more solvents comprise a solvent system that is non-aqueous.

21. The composition of claim 1, wherein the one or more solvents comprise a solvent system that comprises less than 5% w/w water.

22. The composition of claim 1, wherein the molar ratio of total hydroxyl groups and nitrogen-containing groups to N-formylloline of the composition is less than about 10, and the nucleophilicity coefficients of the hydroxyl or nitrogen-containing groups of the composition are less than 0.6 eV, wherein the nitrogen-containing groups are selected from ammonia, a primary amine group, a secondary amine group, or mixtures thereof.

23. A method for controlling one or more insect pests, the method comprising applying to a plant or its surroundings a composition as claimed in claim 1.

24. A composition comprising at least about 10 g/L of one or more loline alkaloids having the structure of Formula [I]:

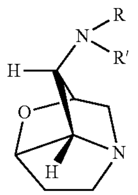

[I]

wherein R═H or $CH_3$ and R'═H, $CH_3$, CHO or $COCH_3$, the one or more loline alkaloids comprising N-formylloline having the structure of Formula [II]:

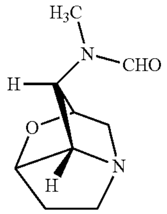

[II]

and one or more solvents; wherein a) the molar ratio of total hydroxyl groups and nitrogen-containing groups to N-formylloline of the composition is less than about 20, or b) the molar ratio of total hydroxyl groups and nitrogen-containing groups to N-formylloline of the composition is greater than about 20, and wherein the nucleophilicity coefficients of the hydroxyl groups or nitrogen-containing groups of the composition are less than about 0.6 eV;

wherein the nitrogen-containing groups are selected from ammonia, a primary amine group, a secondary amine group, or mixtures thereof;

wherein the one or more solvents are polyalkylene glycols having a molecular weight of from 200 to 600, or ethers thereof;

wherein at least about 95% w/w of the total solvents of the composition consists of the one or more solvents.

* * * * *